(12) United States Patent
Xiang et al.

(10) Patent No.: US 11,135,219 B2
(45) Date of Patent: Oct. 5, 2021

(54) METHODS OF TREATING OR PREVENTING ZIKA VIRUS INFECTION

(71) Applicant: NUtech Ventures, Lincoln, NE (US)

(72) Inventors: Shi-hua Xiang, Lincoln, NE (US); Nicholas Palermo, Omaha, NE (US); Asit K. Pattnaik, Lincoln, NE (US); Aryamav ' Pattnaik, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 16/843,450

(22) Filed: Apr. 8, 2020

(65) Prior Publication Data

US 2020/0316059 A1    Oct. 8, 2020

Related U.S. Application Data

(63) Continuation of application No. 16/176,846, filed on Oct. 31, 2018, now abandoned.

(60) Provisional application No. 62/579,495, filed on Oct. 31, 2017.

(51) Int. Cl.
*A61K 31/496* (2006.01)
*A61P 31/14* (2006.01)
*A61K 9/00* (2006.01)

(52) U.S. Cl.
CPC .......... *A61K 31/496* (2013.01); *A61K 9/0019* (2013.01); *A61P 31/14* (2018.01)

(58) Field of Classification Search
CPC ..... A61K 31/496; A61K 9/0019; A61P 31/14; Y02A 50/30
See application file for complete search history.

(56) References Cited

FOREIGN PATENT DOCUMENTS

WO    WO-2004046095 A1 *  6/2004   ........... C07D 231/14
WO    WO-2018136559 A1 *  7/2018   ......... A61K 31/7072

OTHER PUBLICATIONS

Pubchem, "Beclabuvir", Dec. 2, 2010 (Year: 2010).*
Aliota et al., "Zika in the Americas, year 2: What have we learned? What gaps remain? A report from the Global Virus Network," Antivir. Res., 2017, 144:223-246.
Annamalai et al., "Zika Virus Encoding Non-glycosylated Envelop Protein is Attenuated and Defective in Neurovasion", J. Virol., 2017, 91(23):e01348-17.
Avelino-Silva and Martin, "Association between Gullain-Barre syndrome and Zika virus infection", Lancet, 2016, 387(10038):2599.
Baronti et al., "Complete coding sequence of zika virus from a French polynesia outbreak in 2013", Genmome announcements, 2014, 2(3), 2 pages.
Barrows et al., "A Screen of FDA-Approved Drugs for Inhibitors of Zika Virus Infection", Cell Host Microbe, 2016, 20(2):259-270.
Butcher et al., "A mechanism for initiating RNA-dependent RNA polymerization", Nature, 2014, 410(6825):235-240.
Carteaux et al., "Zika Virus Associated with Meningoencephalitis", N. Engl. J. Med., 2016, 374(16):1595-1596.
Cauchemez et al., "Association between Zika virus and microcephaly in French Polynesia, 2013-15: a retrospective study", Lancet, 2016, 387(10033):2125-2132.
Chan et al., "Zika fever and congenital Zika syndrome: An unexpected emerging arboviral disease", J. Infect., 2016, 72(5):507-524.
Che et al., "The development, optimization and validation of an assay for high throughput antiviral drug screening against Dengue virus", Int. J. Clin. Exp., 2009, 2(4):363-373.
Choi et al., "RNA-dependent polymerases from Flaviviridae. Current opinion in structural biology", 2009, 19(6):746-751.
Coyne and Lazear, "Zika virus—reigniting the Torch", Nat. Rev. Microbiol., 2016, 14:707-715.
Cugola et al., "The Brazilian Zika virus strain causes birth defects in experimental models", Nature, 2016, 534(7606):267-271.
Deseda, "Epidemiology of Zika", Curr. Opin. Pediatr., 2017, 29(1):97-101.
Diamond et al., "Mycophenolic acid inhibits dengue virus infection by preventing replication of viral RNA", Virology, 2002, 304(2):211-221.
Dick et al., "Zika virus (I). Isolations and serological specificity", Trans. Roy. Soc. Trop. Med. Hyg., 1952, 46(5):509-520.
D'Ortenzio et al., "Evidence of Sexual Transmission of Zika Virus", The New England Journal of medicine, 2016, 374(22):2195-2198.
Duan et al., "The crystal structure of Zika virus NS5 reveals conserved drug targets", EMBO J., 2017, 36(7):919-933.
Fauci and Morens, "Zika Virus in the Americas—Yet Another Arbovirus Threat", N. Engl. J. Med., 2016, 374(7):601-604.
Godoy et al., "Crystal structure of Zika virus NS5 RNA-dependent RNA polymerase", Nature communications, 2017, 8:14764.
Gulland, "Zika virus is a global public health emergency, declares WHO", BMJ, 2016, 352:i657.
Lazear and Diamond, "Zika Virus: New Clinical Syndromes and Its Emergence in the Western Hemisphere", J. Virol., 2016, 90(10):4864-4875.
Lu et al., "Analysis of Ribonucleotide 5'-Triphosphate Analogs as Potential Inhibitors of Zika Virus RNA-Dependent RNA Polymerase by Using Nonradioactice Polymerase Assays", Antimicrobial agents and chemotherapy, 2017, 61.
Mansuy et al., "Zika virus: high infectious viral load in semen, a new sexually transmitted pathogen", The Lancet Infectious diseases, 2016, 16:405.
Mastrangelo et al., "Ivermectin is a potent inhibitor of flavivirus replication specifically targeting NS3 helicase activity: new prospects for an old drug", Journal of antimicrobial chemotherapy, 2012, 67:1884-1894.
Mecharles et al., "Acute myelitis due to Zika virus infection", Lancet, 2016, 387:1481.
Minor and Diamond, "Zika Virus Pathogenesis and Tissue Tropism", Cell Host Microbe, 2017, 21(2):134-142.

(Continued)

*Primary Examiner* — Sarah Pihonak
(74) *Attorney, Agent, or Firm* — Fish & Richardson P.C.

(57) ABSTRACT

This document relates to methods and materials for treating a mammal having a Zika virus (ZIKV) infection. For example, a composition including one or more non-nucleoside RNA polymerase inhibitors can be administered to a mammal having, or at risk of developing, a ZIKV infection to treat the mammal

17 Claims, 10 Drawing Sheets

Figure 2A:
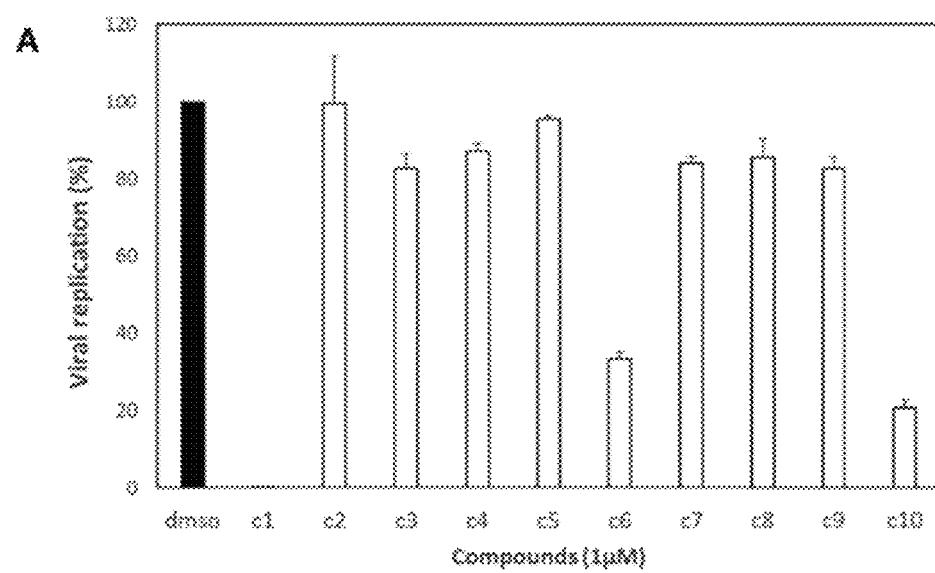
Figure 2B:
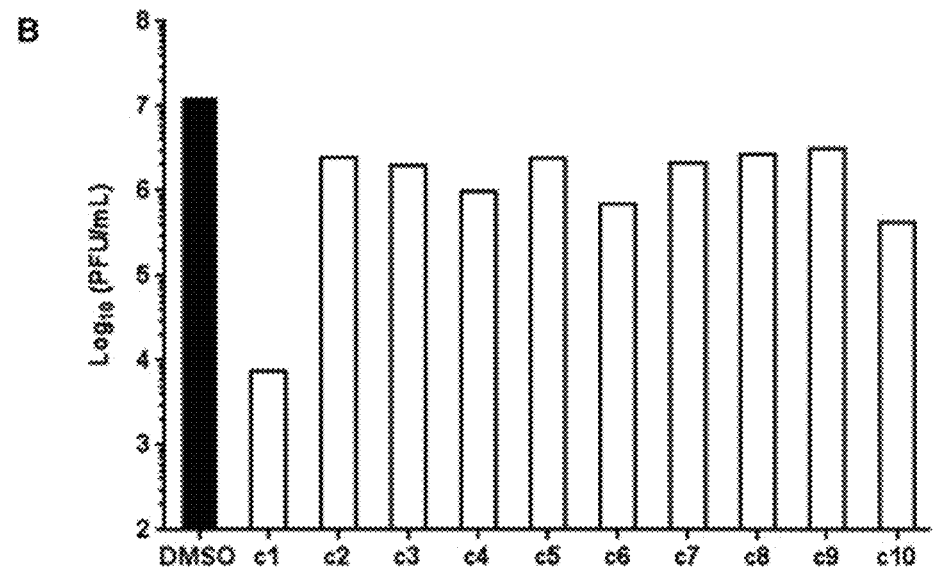
Figure 3A:
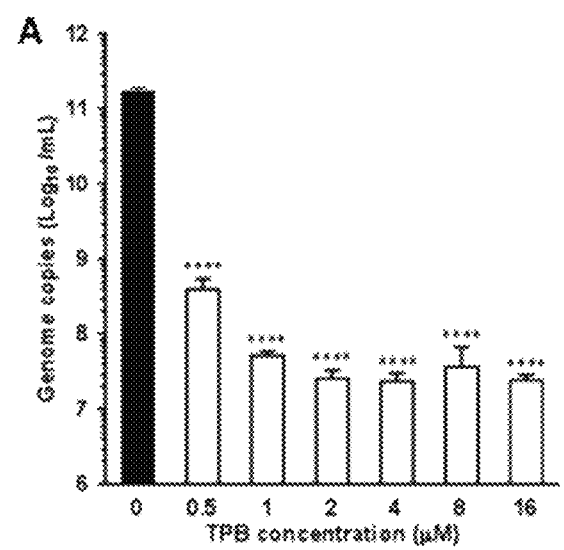
Figure 3B:
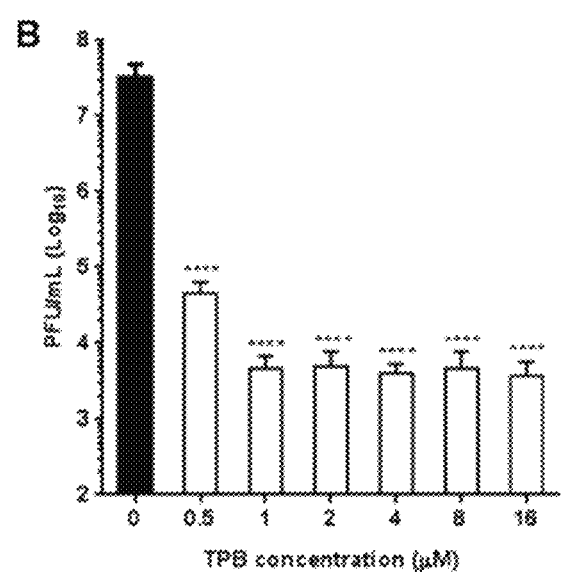
Figure 3C:
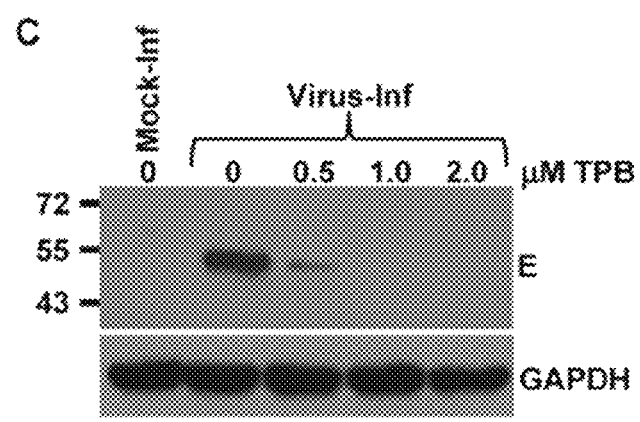
Figure 4A:
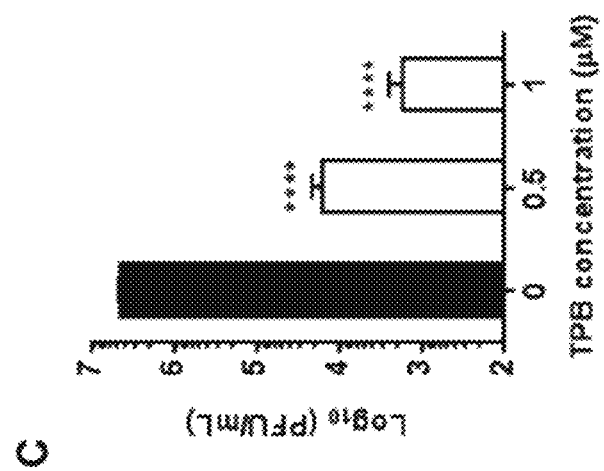
Figure 4B:
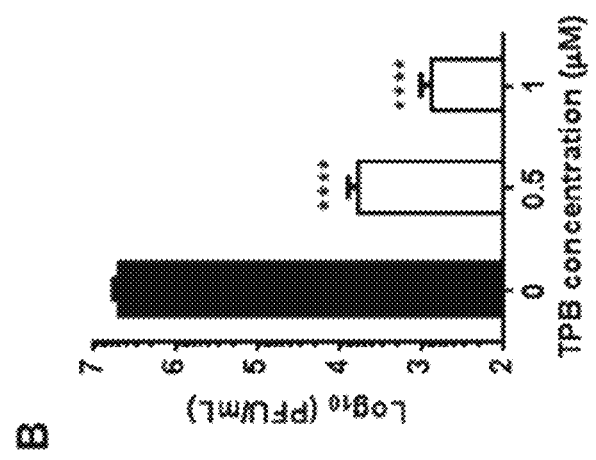
Figure 4C:
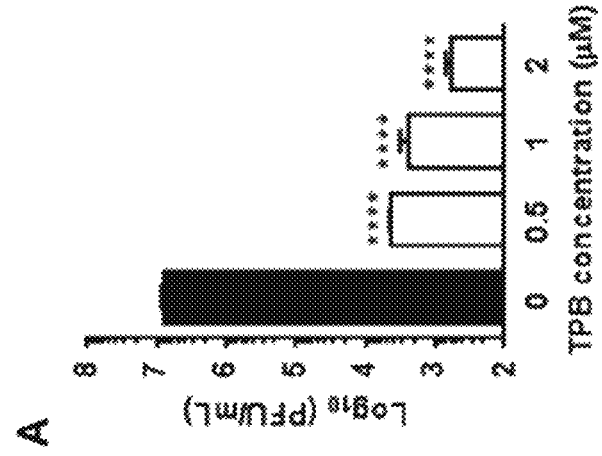
Figure 8:
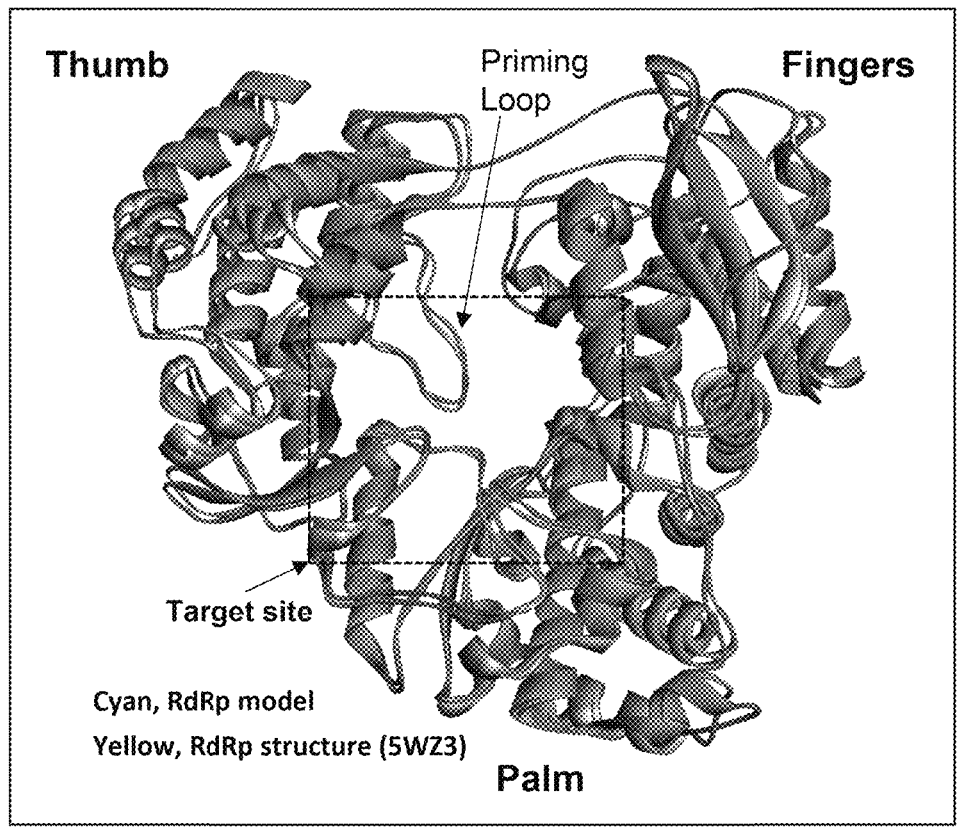

Specification includes a Sequence Listing.

(56) References Cited

OTHER PUBLICATIONS

Mlakar et al., "Zika Virus Associated with Microcephaly", N. Engl. J. Med., 2016, 374(10):951-958.
Moreira et al., "Sexually acquired Zika virus: a systematic review," European Society of Clinical Microbiology and Infectious diseases, 2017, 23, 296-305.
Munoz et al., "Zika Virus-Associated Neurological Disease in the Adult: Guillain-Barré Syndrome, Encephalitis, and Myelitis", Semin. Reprod. Med., 2016, 34(5):273-279.
Nascimento et al., "Zika virus infection-associated acute transient polyneuritis", Neurology, 2017, 88(24):2330-2332.
Ng et al., "Structure-function relationships among RNA-dependent RNA polymerases", Current topics in microbiology and immunology, 2008, 320:137-156.
Parra et al., "Guillain-Barré Syndrome Associated with Zika Virus Infection in Colombia", N. Engl. J. Med., 2016, 375(16):1513-1523.
Perera et al., "Structural proteomics of denuge virus", Current opinion in microbiology, 2008, 11(4):369-377.
PubChem, 3-chloro-N4[444-(thiophene-2-carbonyl)piperazin-1-yl]phenyl]carbannothioy11-1-benzothiophene-2-carboxannide, US National Library of Medicine, publ. Jul. 12, 2005, pp. 1-11.
Ramharack et al., "Zika virus NS5 protein potential inhibitors: an enhanced in silicon approach in drug discovery", Journal of biomolecular structure & dynamics, 2017, 1-16.
Rather et al., "Prevention and Control Strategies to Counter ZIKA Epidemic", Front. Microbiol., 2017, 8:305.
Roos, "Zika Virus—A Public Health Emergency of International Concern", J. Neurol., 2016, 73(12):1395-1396.
Salam et al., "Clinical Trials of Therapeutics for the Prevention of Congenital Zika Virus Disease: Challenges and Potential Solutions", Ann. Intern. Med., 2017, 166(10):725-732.
Shan et al., "Zika Virus: Diagnosis, Therapeutics, and Vaccine", Adv. Infect. Dis., 2016, 2:170-172.
Upadhyay et al., "Crystal structure of full-length Zika virus NS5 protein reveals a conformation similar to Japanese Encephalitis virus NS5", Acta crystallographica, Section F, Structural biology communications, 2017, F73:116-122.
Wang et al., "The structure of Zika virus NS5 reveals a conserved domain conformation", Nature communications, 2017, 8:14763.
Weaver et al., "Zika virus: History, emergence, biology, and prospects for control", Antivir. Res., 2019, 130:69-80.
Xu et. al., Journal of Antimicrobial Chemotherapy, Dec. 20, 2016, Oxford University Press, vol. 72, pp. 727-734.
Yap et al., "Crystal structure of dengue virus RNA-dependent RNA polymerase catalytic domain at 1.85-angstrom resolution", Journal of virology, 2007, 81(9):4753-4765.
Zhao et al., "Structure and function of the Zika virus full-length NS5 protein", Nature communications, 2017, 8:14762.

\* cited by examiner

FIG. 1A
FIG. 1C
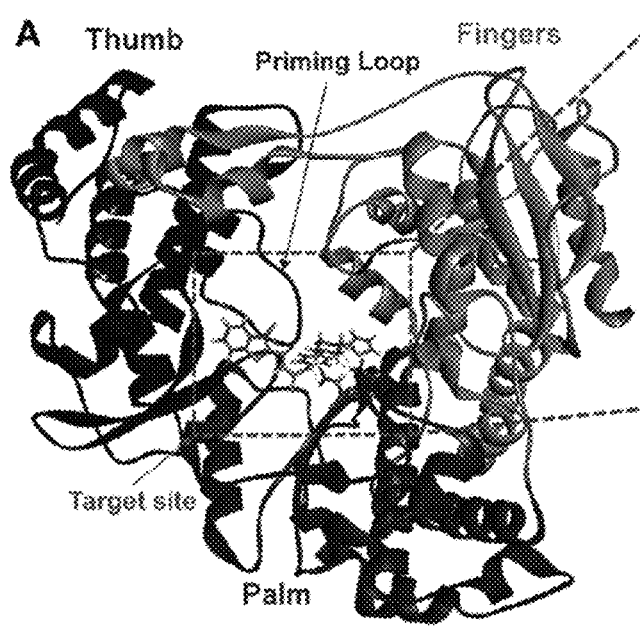
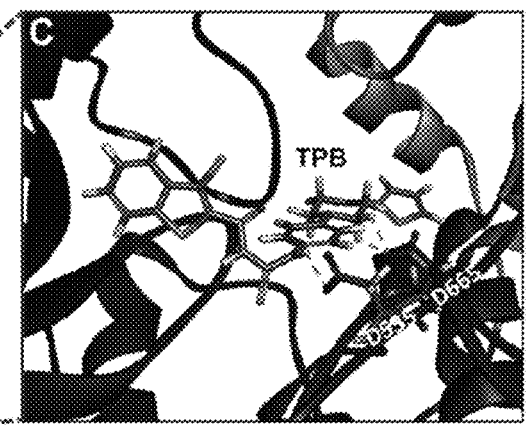
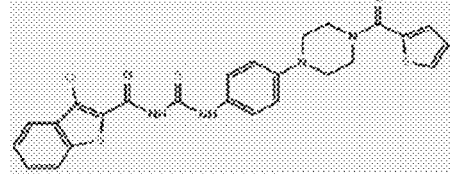
3-chloro-N-[[(4-[4-(3-phenylcarbonyl)-1-piperazinyl]phenyl)amino)
carbonothioyl]-1-benzothiophene-2-carboxamide (TPB).
FIG. 1B
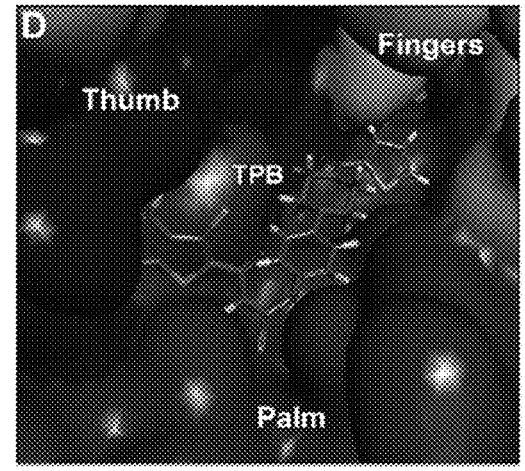
FIG. 1D

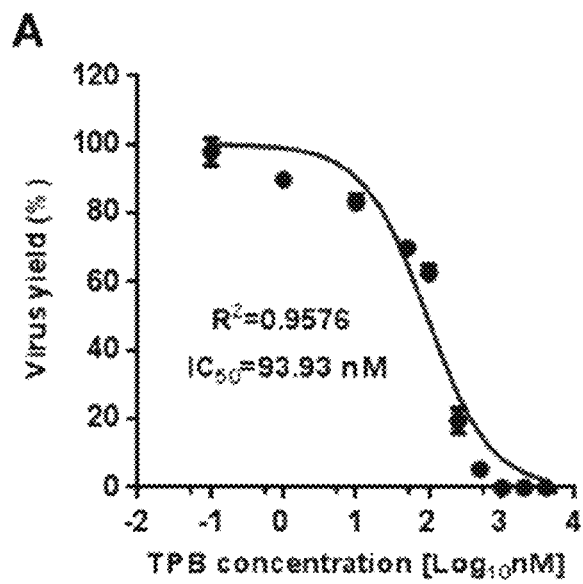
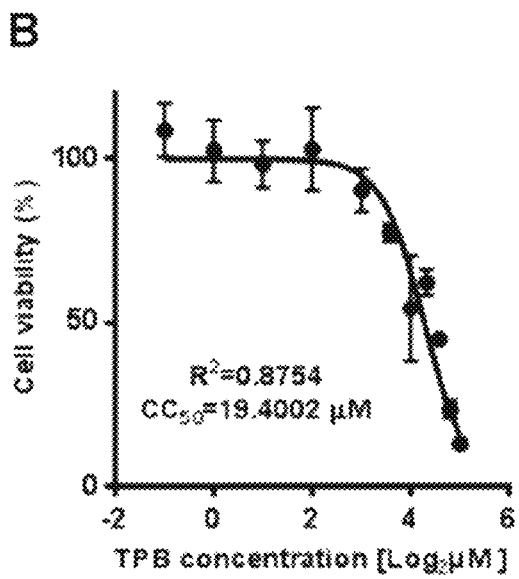
FIG. 5A  FIG. 5B
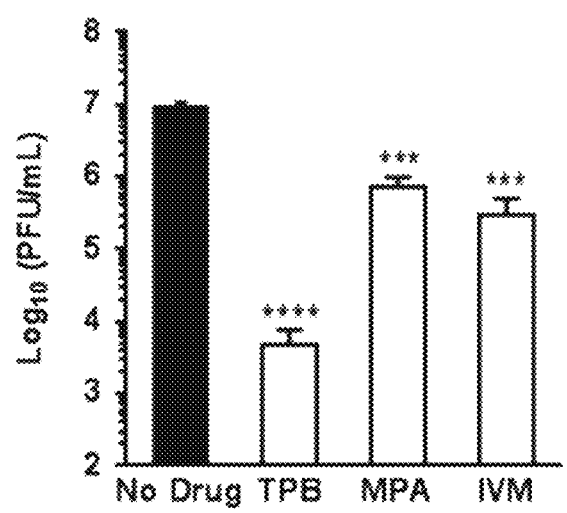
FIG. 6

FIG. 7A
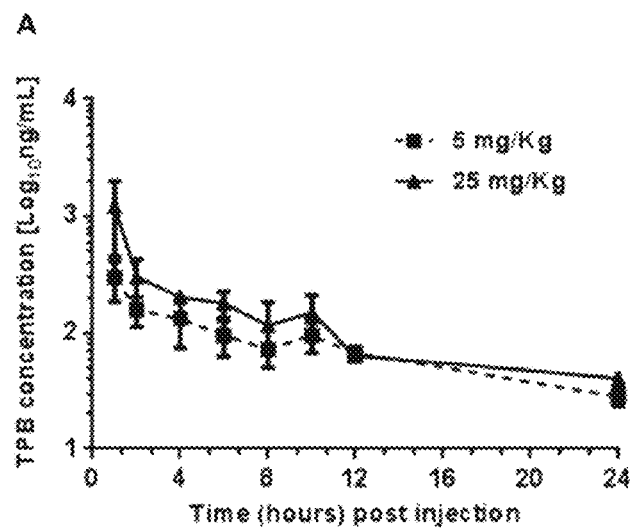
FIG. 7B
FIG. 7C
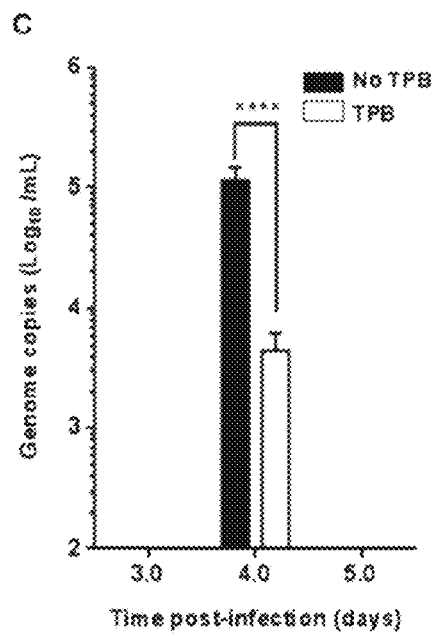
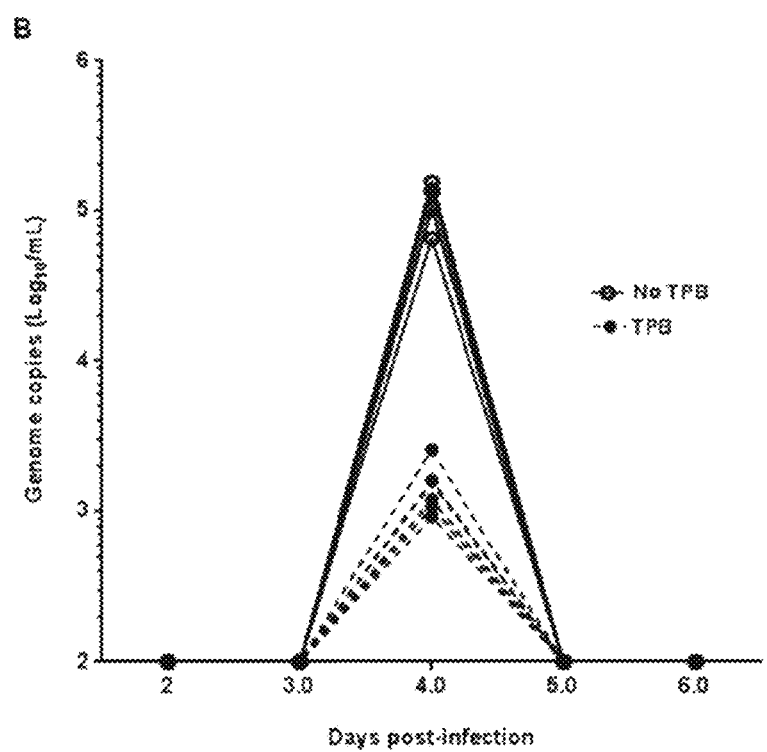
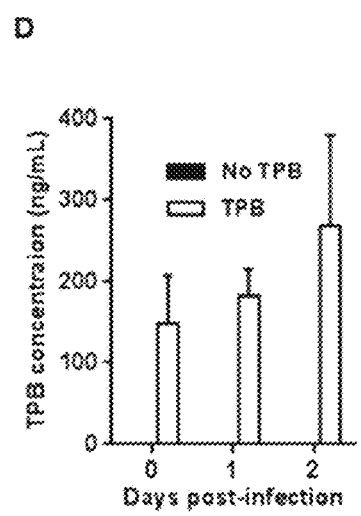
FIG. 7D

| Structure | ID | Mol weight | Mol Name |
|---|---|---|---|
| 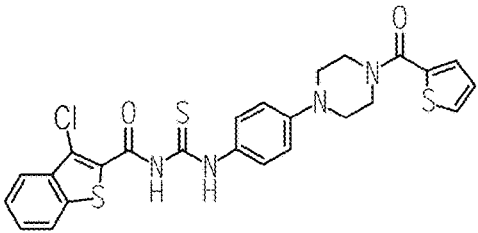 | c1 7723856 | 541.1 | 3-chloro-N-[({4-[4-(2-thienylcarbonyl)-1-piperazinyl]phenyl}amino)carbonothioyl]-1-benzothiophene-2-carboxamide |
| 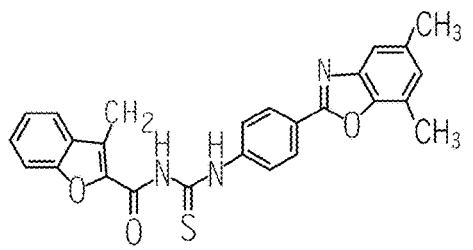 | c2 6508710 | 455.5 | N-({[4-(5,7-dimethyl-1,3-benzoxazol-2-yl)phenyl]amino}carbonothioyl)-3-methyl-1-benzofuran-2-carboxamide |
| 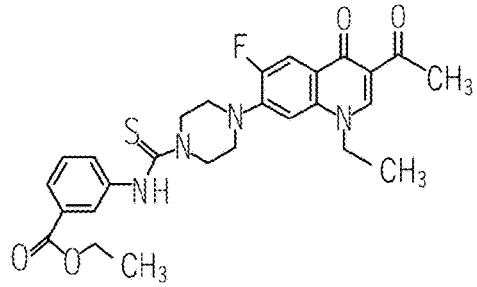 | c3 7505722 | 526.6 | 7-[4-({[3-(ethoxycarbonyl)phenyl]amino}carbonothio piperazinyl]-1-ethyl-6-fluoro-4-oxo-1,4-dihydro-3-quinolinecarboxylic acid |
| 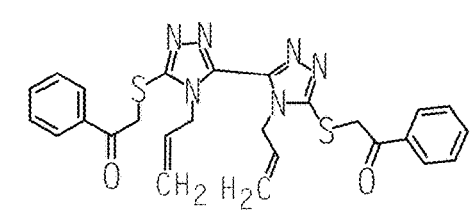 | c4 6872099 | 516.6 | 2,2'-[(4,4'-diallyl-4H,4'H-3,3'-bi-1,2,4-triazole-5,5'-diyl)bis(thio)]bis(1-phenylethanone) |
| 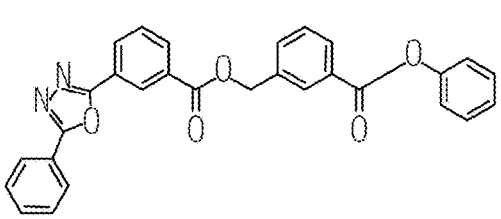 | c5 7893454 | 476.5 | 3-(phenoxycarbonyl)benzyl 3-(5-phenyl-1,3,4-oxadiazol-2-yl)benzoate |

FIG. 10

| | | | |
|---|---|---|---|
| 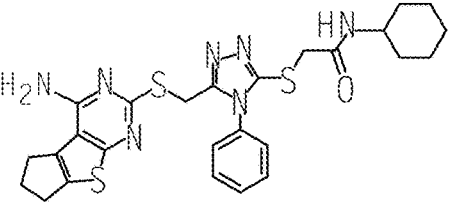 | c6<br>7704013 | 551.7 | 2-[(5-{[4-amino-6,7-dihydro-5H-cyclopenta[4,5]thieno[2,3-d]pyrimidin-2-yl)thio]methyl]-4-phenyl-4H-1,2,4-triazol-3-yl)thio]-N-cyclohexylacetamide |
| 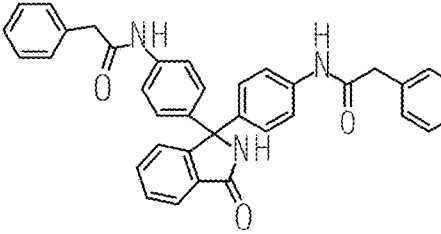 | c7<br>5181035 | 551.6 | N,N'-[(3-oxo-2,3-dihydro-1H-isoindole-1,1-diyl)di-4,1-phenylene]bis(2-phenylacetamide) |
| 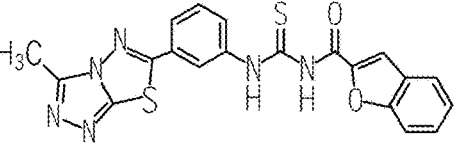 | c8<br>7871281 | 434.5 | N-({[3-(3-methyl[1,2,4]triazolo[3,4-b][1,3,4]thiadiazol-6-yl)phenyl]amino}carbonothioyl)-1-benzofuran-2-carboxamide |
| 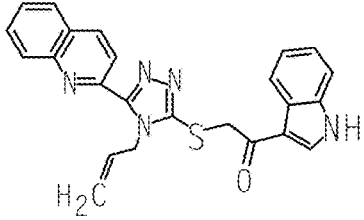 | c9<br>7538200 | 425.5 | 2-{4-allyl-5-(2-quinolinyl)-4H-1,2,4-triazol-3-yl]thio}-1-(1H-indol-3-yl)ethanone |
| 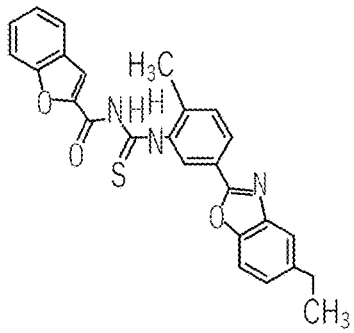 | c10<br>6502337 | 455.5 | N-({[5-(5-ethyl-1,3-benzoxazol-2-yl)-2-methyphenyl]amino}carbonothioyl)-1-benzofuran-2-carboxamide |

FIG. 10 (continued)

SEQUENCE LISTING

<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: synthetic primer

<400> SEQUENCE: 1
ccgctgccca acacaag                                                    17

<210> SEQ ID NO 2
<211> LENGTH: 24
<212> TYPE: DNA
<213> ORGANISM: Artificial Sequence
<220> FEATURE:
<223> OTHER INFORMATION: synthetic primer

<400> SEQUENCE: 2
ccactaacgt tcttttgcag acat                                            24

<210> SEQ ID NO 3
<211> LENGTH: 31
<212> TYPE: DNA
<213> ORGANISM: Artificial Sequence

```
<220> FEATURE:
<223> OTHER INFORMATION: synthetic probe

<400> SEQUENCE: 3
agcctacctt gacaagcaat cagacactca a                              31
```

METHODS OF TREATING OR PREVENTING ZIKA VIRUS INFECTION

CROSS-REFERENCE TO RELATED APPLICATIONS

This application is a continuation application of U.S. patent application Ser. No. 16/176,846, filed Oct. 31, 2018, which claims the benefit of U.S. Patent Application Ser. No. 62/579,495, filed on Oct. 31, 2017. The disclosure of the prior applications are considered part of (and are incorporated by reference in) the disclosure of this application.

BACKGROUND

1. Technical Field

This document relates to methods and materials for treating a mammal having a Zika virus (ZIKV) infection. For example, one or more non-nucleoside RNA polymerase inhibitors can be administered to a mammal having, or at risk of developing, a ZIKV infection to treat the mammal.

2. Background Information

ZIKV, a mosquito-borne pathogen, was originally isolated in Uganda in 1947 (Dick et al., 1952 *Trans. Roy. Soc. Trop. Med. Hyg.* 46:509-520) and only sporadic cases of virus outbreaks in humans were reported in Africa and Asia in the next six decades (Mecharles et al., 2016 *Lancet* 387:1481; Munoz et al., 2016 *Semin. Reprod. Med.* 34:273-279). However, in the past ten years, it has rapidly emerged and spread to the regions of Asia, Europe, and the Americas (Aliota et al., 2017 *Antivir. Res.* 144:223-246; Chan et al., 2016 *J. Infect.* 72:507-524; Deseda, 2017 *Curr. Opin. Pediatr.* 29:97-101; Weaver et al., 2016 *Antivir. Res.* 130:69-80). Although the majority of infections in humans are asymptomatic, recent ZIKV infections have been linked to a variety of congenital disorders including microcephaly and fetal growth restriction (Carteaux et al., 2016 *N. Engl. J. Med.* 374:1595-1596.; Cauchemez et al., 2016 *Lancet* 387: 2125-2132; Chan et al., 2016 *J. Infect.* 72:507-524; Coyne and Lazear, 2016 *Nat. Rev. Microbiol.* 14:707-715; Cugola et al., 2016 *Nature* 534:267-271; Lazear and Diamond, 2016 *J. Virol.* 90:4864-4875; Miner and Diamond, 2017 *Cell Host Microbe* 21:134-142; and Mlakar et al., 2016 *N. Engl. J. Med.* 374:951-958) as well as Guillain-Barre syndrome in adults (Avelino-Silva and Martin, 2016 *Lancet* 387:2599; Nascimento et al., 2017 *Neurology* 88:2330-2332; and Parra et al., 2016 *N. Engl. J. Med.* 375:1513-1523). These severe consequences and the large-scale spreading of the virus have imposed a significant threat to human health worldwide (Fauci and Morens, 2016 *N. Engl. J. Med.* 374:601-604; Gulland, 2016 *BMJ* 352:i657; Roos, 2016 *J. Neurol.* 73:1395-1396). So far, no vaccine or drug for preventing or treating this viral disease is available (Shan et al., 2016 *Adv. Infect. Dis.* 2:170-172). Therefore, it is urgent to develop countermeasures against this viral epidemic (Rather et al., 2017 *Front. Microbiol.* 8:305; Salam et al., 2017 *Ann. Intern. Med.* 166:725-732).

SUMMARY

ZIKV has become a major human health concern globally due to its association with congenital abnormalities and neurological diseases.

This document provides methods and materials for treating a mammal having, or at risk of developing, ZIKV in its bloodstream (e.g., ZIKV viremia). In some cases, ZIKV viremia can lead to a ZIKV infection. For example, one or more non-nucleoside RNA polymerase inhibitors (e.g., 3-chloro-N-[({4-[4-(2-thienylcarbonyl)-1-piperazinyl]phenyl}amino)carbonothioyl]-1-benzothiophene-2-carboxamide (TPB)) can be administered to a mammal having, or at risk of developing, ZIKV viremia to treat the mammal. In some cases, one or more non-nucleoside RNA polymerase inhibitors can inhibit ZIKV replication (e.g., within in a cell in a mammal). In some cases, one or more non-nucleoside RNA polymerase inhibitors can reduce ZIKV viremia in a mammal.

As demonstrated herein, TPB inhibited ZIKV replication at sub-micromolar concentrations (e.g., the half-maximal inhibitory concentration ($IC_{50}$) and the cytotoxicity concentration ($CC_{50}$) of TPB in Vero cells were 94 nM and 19.4 µM, respectively, yielding a high selective index 50 ($SI_{50}$) of 206). Without being bound by theory, molecular docking analysis suggested that TPB binds to the catalytic active site of the ZIKV RNA-dependent RNA-polymerase (RdRp) and therefore likely blocks the viral RNA synthesis by an allosteric effect. Also as demonstrated herein, TPB reduced ZIKV viremia significantly in immunocompetent mice. The ability to inhibit ZIKV replication can reduce ZIKV viremia providing a unique and unrealized opportunity to treat and/or prevent ZIKV infections. For example, TPB can be used to treat and/or prevent ZIKV infections.

In general, one aspect of this document features methods for treating mammals having a ZIKV infection. The methods can include, or consist essentially of, administering to a composition including a non-nucleoside RNA polymerase inhibitor to a mammal having a ZIKV infection to treat the mammal. The mammal can be a human. The non-nucleoside RNA polymerase inhibitor can bind to a catalytic active site of an RdRp of a ZIKV to inhibit ZIKV replication. The non-nucleoside RNA polymerase inhibitor can be TPB. The non-nucleoside RNA polymerase inhibitor can have an $IC_{50}$ of from about 10 nM to about 200 nM. The non-nucleoside RNA polymerase inhibitor can have a $CC_{50}$ of from about 15 µM to about 25 µM. The non-nucleoside RNA polymerase inhibitor can have a $SI_{50}$ of about 206. The administering step can be performed prior to the mammal being infected with the ZIKV or after the mammal being infected with the ZIKV. The administering step can be performed prior to the mammal being infected with the ZIKV and after the mammal being infected with the ZIKV. The non-nucleoside RNA polymerase inhibitor can be administered intraperitoneally, intravenously, intramuscularly, or subcutaneously.

In another aspect, this document features methods for method of preventing microcephaly in a fetus. The methods can include, or consist essentially of, administering a composition including a non-nucleoside RNA polymerase inhibitor to a mammal pregnant with a fetus, where the pregnant mammal has a ZIKV infection. The mammal can be a human. The non-nucleoside RNA polymerase inhibitor can bind to a catalytic active site of an RdRp of a ZIKV to inhibit ZIKV replication. The non-nucleoside RNA polymerase inhibitor can be TPB. The non-nucleoside RNA polymerase inhibitor can have an $IC_{50}$ of from about 10 nM to about 200 nM. The non-nucleoside RNA polymerase inhibitor can have a $CC_{50}$ of from about 15 µM to about 25 µM. The non-nucleoside RNA polymerase inhibitor can have a $SI_{50}$ of about 206. The non-nucleoside RNA polymerase inhibitor can be administered intraperitoneally, intravenously, intramuscularly, or subcutaneously.

In another aspect, this document features methods for treating adult mammals having Guillain-Barre syndrome. The methods can include, or consist essentially of, administering a composition including a non-nucleoside RNA polymerase inhibitor to a mammal having a ZIKV infection and having Guillain-Barre syndrome to treat the mammal. The mammal can be a human. The non-nucleoside RNA polymerase inhibitor can bind to a catalytic active site of an RdRp of a ZIKV to inhibit ZIKV replication. The non-nucleoside RNA polymerase inhibitor can be TPB. The non-nucleoside RNA polymerase inhibitor can have an $IC_{50}$ of from about 10 nM to about 200 nM. The non-nucleoside RNA polymerase inhibitor can have a $CC_{50}$ of from about 15 μM to about 25 μM. The non-nucleoside RNA polymerase inhibitor can have a $SI_{50}$ of about 206. The non-nucleoside RNA polymerase inhibitor can be administered intraperitoneally, intravenously, intramuscularly, or subcutaneously.

In another aspect, this document features compositions for reducing ZIKV viremia within a mammal. The compositions include a non-nucleoside RNA polymerase inhibitor. The non-nucleoside RNA polymerase inhibitor can be TPB. The non-nucleoside RNA polymerase inhibitor can bind to a catalytic active site of an an RdRp of a ZIKV. The non-nucleoside RNA polymerase inhibitor can have an $IC_{50}$ of from about 10 nM to about 200 nM. The non-nucleoside RNA polymerase inhibitor can have a $CC_{50}$ of from about 15 μM to about 25 μM. The non-nucleoside RNA polymerase inhibitor can have a $SI_{50}$ of about 206. The composition also can include a pharmaceutically acceptable carrier.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 1A-1D show a structure-based screening of inhibitors of ZIKV targeting the viral RNA-dependent RNA-polymerase (RdRp). (FIG. 1A) Structure of ZIKV RdRp generated by homology modeling. The three subdomains are colored individually, Fingers (cyan), Thumb (blue) and Palm (red). The catalytic active site and the priming loop are labeled. Docking of TPB on the active site of RdRp and the contacts with the two aspartic residues (D535 and D665) along with the three hydrogen bonds are indicated. (FIG. 1B) The chemical structure of TPB (molecular weight of 541.108). (FIG. 1C) A larger view of the boxed area in A is shown for clarity. (FIG. 1D) The space-filing model of the boxed area in A is shown along with the bound TPB. TPB binding at the palm subdomain is shown.

FIGS. 2A-2B show inhibition of ZIKV replication by the top 10 lead compounds. (FIG. 2A) Viral genome copies in the supernatants of cells infected with PRVABC59 virus in the presence of 1 μM concentration of the ten compounds (c1-c10) or with vehicle (DMSO) alone for 72 hours. The data are expressed as % of DMSO-treated control. The experiment was done in triplicate and bars represent±SEM. (FIG. 2B) Infectious virus titers in the supernatant of cells infected with the virus and incubated with 1 μM concentration of the compounds or with vehicle (DMSO) alone for 96 hours.

FIGS. 3A-3C show validation of the antiviral effect of TPB in the μM range. (FIG. 3A) Cells infected with PRV-ABC59 virus were incubated in the presence of various concentrations of TPB for 96 hours. Culture supernatants were titrated for viral genome copies (FIG. 3A) and infectious virus (FIG. 3B). Data are from three independent experiments with error bars showing±SEM. Statistical analysis was performed using unpaired two-tailed Student's t-test to determine significance of difference. **, $p \leq 0.001$. (FIG. 3**C) Western blot analysis of E protein expression in virus-infected cells in the presence of various concentrations of TPB. Relative mobility of molecular mass markers are shown on the left.

FIGS. 4A-4C shows TPB inhibition of ZIKV is strain and cell-type independent. (FIG. 4A) Inhibition of MR766 virus by TPB. The experiments were conducted as in FIG. 3B and data from three independent experiments are presented with error bars representing SEM. PRVABC59 virus growth in HTR-8 (FIG. 4B) and NTERRA (FIG. 4C) cell lines in the presence of TPB. Data from three independent experiments are presented with error bars showing ±SEM. Statistical analysis was performed using unpaired two-tailed Student's t-test to determine significance of difference. ****, $p \leq 0.001$.

FIGS. 5A-5B show $IC_{50}$ and $CC_{50}$ of TBP. (FIG. 5A) Vero cells in triplicate were infected with PRVABC59 virus and incubated with various concentrations of TPB as shown. Infectious virus titers in the supernatants of the cells at 96 hours post-infection were determined by plaque assay and virus yield was expressed as % of TPB-untreated control. Non-linear regression analysis was employed to determine the $IC_{50}$. (FIG. 5B) Vero cells in triplicate were treated with TPB at various concentrations for four days and cell viability was measured based on ATP assay. The luminescence signals were measured at 420 nm using a Microplate Luminometer. Non-linear regression analysis of the data was employed to determine the $CC_{50}$.

FIG. 6 shows a comparison of TPB inhibitory activity with mycophenolic acid (MPA) and Ivermectin (IVM). Vero cells were infected with PRVABC59 virus and incubated with TPB (1 μM), MPA (1 μM) and IVM (10 μM). Culture supernatants were collected at 96 hours post-infection and assayed for infectious virus. Data presented are from three independent experiments with error bars showing ±SEM. Statistical analysis was performed using unpaired two-tailed Student's t-test to determine significance of difference. *$p \leq 0.01$; **$p \leq 0.001$.

FIGS. 7A-7D shows inhibitory efficacy of TPB in mice. (FIG. 7A) Pharmacokinetics (PK) analysis of TPB in mice using two different doses as shown. (FIG. 7B) Genome copies at various days post-infection in the plasma of individual mice treated without (continuous lines) or with (discontinuous lines) TPB. (FIG. 7C) Data from the mice groups in panel B. Error bars show ±SEM. Statistical analysis was performed using unpaired two-tailed Student's t-test to determine significance of difference. **, $p \leq 0.001$. (FIG. 7**D) TPB mean concentrations in mice plasma at various days post-infection. Error bars show±SEM.

FIG. 8 shows model of superimposed structures of ZIKV RdRp. Cyan, RdRp structure derived from homology modeling; yellow, crystal structure of RdRp (PDB: 5WZ3). Various domains are identified.

Figures 9A, 9B:
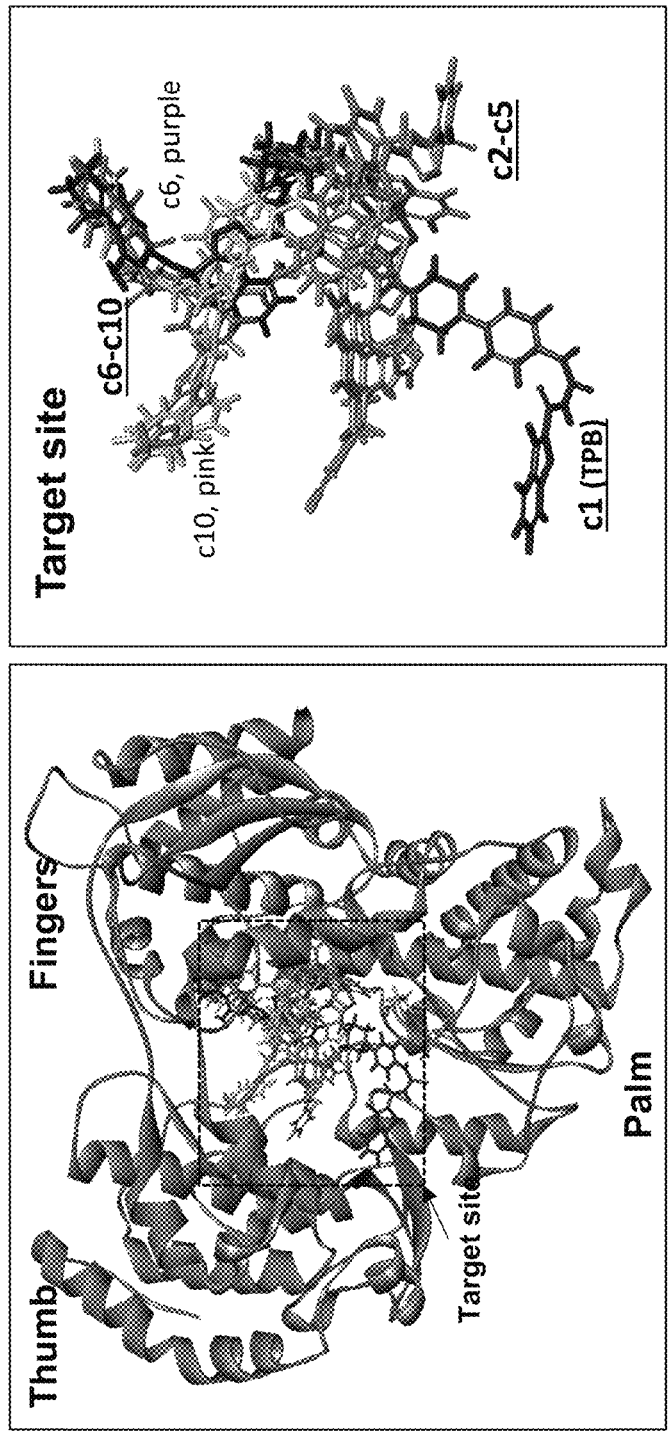

FIGS. 9A-9B shows models of an alignment of compounds within the target site of the ZIKV RdRp (FIG. 9A) and an enlarged view of the positioning of the compounds (FIG. 9B) in the target site of the RdRp.

FIG. 10 contains exemplary non-nucleoside RNA polymerase inhibitors.

DETAILED DESCRIPTION

This document provides methods and materials for treating a mammal having, or at risk of developing ZIKV viremia (e.g., a ZIKV infection). In some cases, this document provides compositions (e.g., pharmaceutical compositions such as vaccines) including one or more non-nucleoside RNA polymerase inhibitors (e.g., TPB). In some cases, this document provides methods for using one or more non-nucleoside RNA polymerase inhibitors provided herein to treat a mammal having, or at risk of having, a ZIKV infection. For example, one or more non-nucleoside RNA polymerase inhibitors can be administered to a mammal (e.g., a human) having, or at risk of developing, a ZIKV infection to treat the mammal. In some cases, one or more non-nucleoside RNA polymerase inhibitors can inhibit ZIKV replication (e.g., within in a cell in a mammal). In some cases, one or more non-nucleoside RNA polymerase inhibitors can reduce ZIKV viremia in a mammal. One or more non-nucleoside RNA polymerase inhibitors can be administered to a mammal to protect the mammal from a ZIKV infection (e.g., prior to exposure to a ZIKV) and/or to treat the mammal (e.g., after exposure to a ZIKV).

Any appropriate mammal (e.g., a mammal having, or at risk of developing, ZIKV viremia) can be treated as described herein. In some cases, a mammal can have, or can be at risk of developing, a ZIKV infection. In some cases, a mammal can carry ZIKV without developing ZIKV infection. Examples of mammals that can be treated as described herein (e.g., by administering one or more non-nucleoside RNA polymerase inhibitors such as TPB to the mammal) include, without limitation, humans, non-human primates (e.g., monkeys), dogs, cats, horses, cows, pigs, sheep, mice, rats, horses, cows, carabaos (water buffaloes), goats, ducks, and bats. For example, a human having, or at risk of developing, ZIKV viremia can be treated by administering one or more non-nucleoside RNA polymerase inhibitors (e.g., TPB) to that human. In some cases, a mammal can be a pregnant mammal (e.g., pregnant human). When a mammal is a pregnant human, the pregnant human can be in any stage of pregnancy (e.g., first trimester, second trimester, or third trimester).

When treating a mammal (e.g., a human) having, or at risk of developing, ZIKV viremia (e.g., a ZIKV infection) as described herein (e.g., by administering one or more non-nucleoside RNA polymerase inhibitors such as TPB to the mammal), the mammal can be any appropriate age. In some cases, a mammal can be an adult. For example, when a mammal is a human, an adult human can be about 18 years of age or older (e.g., about 20 years of age, about 30 years of age, about 40 years of age, about 50 years of age, about 60 years of age, about 65 years of age, about 70 years of age, or about 75 years of age or older). For example, when a mammal is a human, an adult human can be from about 18 years of age to about 80 years of age (e.g., from about 18 years of age to about 60 years of age, from about 18 years of age to about 40 years of age, from about 25 years of age to about 80 years of age, from about 40 years of age to about 80 years of age, from about 60 years of age to about 80 years of age, from about 20 years of age to about 60 years of age, or from about 30 years of age to about 50 years of age). In some cases, a mammal can be a juvenile. For example, when a mammal is a human, a juvenile human can be no more than about 18 years old. For example, a human adolescents can be from about 1 year of age to about 18 years of age (e.g., from about 1 year of age to about 15 years of age, from about 1 year of age to about 10 years of age, from about 1 year of age to about 5 years of age, from about 5 years of age to about 18 years of age, from about 10 years of age to about 18 years of age, or from about 5 years of age to about 15 years of age). In some cases, a mammal can be a newborn. For example, when a mammal is a human, a newborn human from about birth to about 1 year of age. In some cases, a mammal can be a fetus. For example, when a mammal is a human, a fetus can be in utero (e.g., being carried by a human pregnant with the fetus).

When treating a mammal (e.g., a human) having, or at risk of developing, ZIKV viremia (e.g., a ZIKV infection) as described herein (e.g., by administering one or more non-nucleoside RNA polymerase inhibitors such as TPB to the mammal), the ZIKV can be any type of ZIKV. A ZIKV can be from any lineage of ZIKV. A ZIKV can be from any clade of ZIKV. A ZIKV can be any strain of ZIKV. In some cases, a ZIKV can be a latent ZIKV. In some cases, a ZIKV can be an infectious ZIKV. Examples of ZIKVs include, without limitation, East African ZIKV, West African ZIKV, Asian ZIKV, and South American ZIKV.

In some cases, methods described herein can include identifying a mammal (e.g., a human) as having a ZIKV infection. Any appropriate method can be used to identify a mammal having a ZIKV infection. For example, the presence of a ZIKV in a sample obtained from a mammal can be detected in a sample obtained from a mammal, where the presence of a ZIKV can indicate that the mammal has a ZIKV infection. In some cases, the presence of a ZIKV genome, or a portion thereof, in a sample obtained from a mammal can be used to identify that mammal (e.g., a human) as having a ZIKV infection. In some cases, the presence of one or more ZIKV polypeptides in a sample obtained from a mammal can be used to identify that mammal (e.g., a human) as having a ZIKV infection. Any appropriate sample can be assessed to detect the presence of a ZIKV genome, or a portion thereof, and/or the presence of one or more ZIKV polypeptides. For example, biological samples such as fluid samples (e.g., blood (e.g., whole blood, plasma, and serum), urine, breast milk, saliva, amniotic fluid, cerebral spinal fluid, or semen) or tissue samples (e.g., placenta tissue samples) can be obtained from a mammal and assessed for the presence the presence of a ZIKV genome, or a portion thereof, and/or the presence of one or more ZIKV polypeptides. Any appropriate method can be used to detect the presence the presence of a ZIKV genome, or a portion thereof. For example, polymerase chain reaction (PCR) techniques), sequencing techniques, and/or Southern blotting can be used to detect the presence of a ZIKV genome, or a portion thereof, in a sample obtained from a mammal. Any appropriate method can be used to detect the presence the presence of one or more ZIKV polypeptides. For example, western blotting techniques, enzyme-linked immunosorbent assays (ELISAs), and/or real-time PCR can be used to detect the presence of one or more ZIKV polypeptides in a sample obtained from a mammal.

In some cases, methods described herein can include identifying a mammal (e.g., a human) as being at risk of developing ZIKV viremia (e.g., a ZIKV infection). For example, a mammal undergoing, or scheduled to undergo, exposure to one or more mammals having ZIKV viremia can be at risk of developing ZIKV viremia. In some cases, a mammal having physical contact (e.g., sexual contact) with one or more mammals having ZIKV viremia can be at risk of developing ZIKV viremia (e.g., a ZIKV infection). In some cases, a mammal living in or moving to an area where one or more mammals having ZIKV viremia are present can be at risk of developing ZIKV viremia (e.g., a ZIKV infection). In some cases, a mammal scheduled to travel to an area where one or more mammals having ZIKV viremia are present can be at risk of developing ZIKV viremia (e.g., a ZIKV infection). In some cases, a mammal that has been bitten, or is at risk of being bitten by an animal that carries a ZIKV virus (e.g., a mosquito) can be at risk of developing ZIKV viremia (e.g., a ZIKV infection). In some cases, a fetus within a pregnant mammal with ZIKV viremia can be at risk of developing ZIKV viremia (e.g., a ZIKV infection).

A mammal (e.g., a human) identified as having, or as being at risk of developing, ZIKV viremia (e.g., a ZIKV infection), can be administered, or instructed to self-administer, one or more non-nucleoside RNA polymerase inhibitors. For example, one or more non-nucleoside RNA polymerase inhibitors can be administered to a mammal in need thereof (e.g., a mammal having, or at risk of developing, ZIKV viremia). A non-nucleoside RNA polymerase inhibitor can be any appropriate non-nucleoside RNA polymerase inhibitor. A non-nucleoside RNA polymerase inhibitor can be a chemically synthesized non-nucleoside RNA polymerase inhibitor. A non-nucleoside RNA polymerase inhibitor can be a commercially obtained non-nucleoside RNA polymerase inhibitor. Examples of non-nucleoside RNA polymerase inhibitors that can be used as described herein (e.g., to treat a mammal having, or at risk of developing, ZIKV viremia) include, without limitation, non-nucleoside RNA polymerase inhibitors shown in FIG. 10 (e.g., TPB, C1, C2, C3, C4, C5, C6, C7, C8, C9, and C10). In some cases, a non-nucleoside RNA polymerase inhibitor can be TPB. In cases where a non-nucleoside RNA polymerase inhibitor is TPB, the TPB can be a derivative of TPB. As used herein, a derivative of a non-nucleoside RNA polymerase can be any structurally derived compound that maintains the ability to inhibit a non-nucleoside RNA polymerase. For example, a mammal having, or at risk of developing, ZIKV viremia can be administered or can self-administer TPB.

A non-nucleoside RNA polymerase inhibitor (e.g., TPB) can inhibit ZIKV replication. In some cases, a non-nucleoside RNA polymerase inhibitor can inhibit transcription of a ZIKV coding sequence (e.g., coding sequence encoding a ZIKV polymerase such as the RdRp polymerase gene). In some cases, a non-nucleoside RNA polymerase inhibitor can inhibit function of a ZIKV polypeptide (e.g., a ZIKV polymerase such as the RdRp polymerase). For example, when a non-nucleoside RNA polymerase inhibitor is TPB, the TPB can inhibit function of the RdRp polymerase. In some cases, TPB can target (e.g., bind to) a catalytic active site of the RdRp polymerase to inhibit ZIKV replication.

A non-nucleoside RNA polymerase inhibitor can be a potent inhibitor (e.g., a potent ZIKV inhibitor). For example, when a non-nucleoside RNA polymerase inhibitor is TPB, the TPB can inhibit a ZIKV (e.g., inhibit ZIKV replication) at sub-micromolar concentrations. In some cases, the inhibitory concentration 50 ($IC_{50}$) of TPB can from about 10 nM to about 200 nM (e.g., from about 10 nM to about 175 nM, from about 10 nM to about 150 nM, from about 10 nM to about 125 nM, from about 10 nM to about 100 nM, from about 10 nM to about 75 nM, from about 10 nM to about 60 nM, from about 10 nM to about 50 nM, from about 10 nM to about 40 nM, from about 10 nM to about 30 nM, from about 10 nM to about 20 nM, from about 25 nM to about 200 nM, from about 50 nM to about 200 nM, from about 70 nM to about 200 nM, from about 90 nM to about 200 nM, from about 100 nM to about 200 nM, from about 125 nM to about 200 nM, from about 150 nM to about 200 nM, from about 175 nM to about 200 nM, from about 25 nM to about 175 nM, from about 50 nM to about 150 nM, from about 75 nM to about 125 nM, from about 50 nM to about 100 nM, from about 100 nM to about 150 nM, from about 30 nM to about 80 nM, from about 50 nM to about 70 nM, or from about 85 nM to about 95 nM). For example, the $IC_{50}$ of TPB can be about 94 nM.

A non-nucleoside RNA polymerase inhibitor can have low toxicity (e.g., cellular toxicity or cytotoxicity). For example, when a non-nucleoside RNA polymerase inhibitor is TPB, the TPB can have sub-micromolar cytotoxicity concentrations. In some cases, the cellular cytotoxicity concentration 50 ($CC_{50}$) of TPB can be from about 15 μM to about 25 μM. For example, the $CC_{50}$ of TPB can be about 19.4 μM.

A non-nucleoside RNA polymerase inhibitor can have high selectivity (e.g., can be selective for a ZIKV). A selective index 50 ($SI_{50}$) can be determined using the formula $CC_{50}/IC_{50}$. For example, when a non-nucleoside RNA polymerase inhibitor is TPB, the TPB can have a high $SI_{50}$. In some cases, the $SI_{50}$ of TPB can be from about 150 to about 250. For example, the $SI_{50}$ of TPB can be about 206.

When treating a mammal having, or at risk of developing, ZIKV viremia (e.g., a ZIKV infection), one or more non-nucleoside RNA polymerase inhibitors (e.g., TPB) can be administered to the mammal at any appropriate time. For example, when a mammal has ZIKV viremia, one or more non-nucleoside RNA polymerase inhibitors can be administered before, during (e.g., concurrent with), and/or after one or more symptoms of a ZIKV infection are producing or showing (e.g., after a ZIKV infection has developed). In some cases, when a mammal has ZIKV viremia, one or more non-nucleoside RNA polymerase inhibitors can be administered before one or more symptoms of a ZIKV infection producing or showing no symptoms (e.g., when the mammal is asymptomatic and/or prior to a ZIKV infection developing). For example, when a mammal at risk of developing ZIKV viremia (e.g., a ZIKV infection) is undergoing, or scheduled to undergo, exposure to one or more mammals having ZIKV viremia (e.g., a ZIKV infection), one or more non-nucleoside RNA polymerase inhibitors can be administered before, during (e.g., concurrent with), and/or after the exposure.

One or more non-nucleoside RNA polymerase inhibitors (e.g., TPB) can be administered to a mammal in need thereof (e.g., a mammal having, or at risk of developing, ZIKV viremia) by any appropriate route. Administration can be local or systemic. Examples of routes of administration include, without limitation, intraperitoneal, intravenous, intramuscular, subcutaneous, oral, intranasal, inhalation, transdermal, and parenteral administration. For example, one or more non-nucleoside RNA polymerase inhibitors can be administered intraperitoneally to a mammal (e.g., a human).

When treating a mammal having, or at risk of developing, ZIKV viremia (e.g., a ZIKV infection), the treatment can include the administration of a therapeutically effective amount of one or more non-nucleoside RNA inhibitors. The terms "effective amount" and "therapeutically effective amount" refer to that amount of one or more non-nucleoside RNA inhibitors sufficient to result in a therapeutic effect. For example, a therapeutic effect of treating a mammal having, or at risk of developing, ZIKV viremia can include, without limitation, inhibition of ZIKV replication, reduction or elimination of ZIKV viremia, and/or amelioration (e.g., reduction or elimination) of one or more symptoms of a ZIKV infection.

In some cases, treating a mammal having, or at risk of developing, ZIKV viremia (e.g., a ZIKV infection) as described herein (e.g., by administering one or more non-nucleoside RNA polymerase inhibitors such as TPB to the mammal) can be effective to inhibit ZIKV replication. For example, administering one or more non-nucleoside RNA polymerase inhibitors to a mammal can be effective to inhibit ZIKV replication within in one or more cells in that mammal. Any appropriate method can be used to determine whether or not ZIKV replication has been inhibited. For example, quantitative RT-PCR (RT-qPCR) and/or ELISAs can be used to determine whether or not ZIKV replication has been inhibited.

In some cases, treating a mammal having, or at risk of developing, ZIKV viremia (e.g., a ZIKV infection) as described herein (e.g., by administering one or more non-nucleoside RNA polymerase inhibitors such as TPB to the mammal) can be effective to reduce or eliminate ZIKV viremia. For example, administering one or more non-nucleoside RNA polymerase inhibitors to a mammal can be effective to reduce ZIKV viremia within that mammal.

In some cases, administering one or more non-nucleoside RNA polymerase inhibitors to a mammal having ZIKV viremia can be effective to reduce ZIKV viremia by from about 40-fold to about 1000-fold (e.g., from about 50-fold to about 1000-fold, from about 80-fold to about 1000-fold, from about 100-fold to about 1000-fold, from about 300-fold to about 1000-fold, from about 500-fold to about 1000-fold, from about 700-fold to about 1000-fold, from about 800-fold to about 1000-fold, from about 900-fold to about 1000-fold, from about 40-fold to about 900-fold, from about 40-fold to about 700-fold, from about 40-fold to about 500-fold, from about 40-fold to about 200-fold, from about 40-fold to about 100-fold, from about 50-fold to about 900-fold, from about 200-fold to about 800-fold, from about 500-fold to about 700-fold, from about 100-fold to about 400-fold, from about 300-fold to about 600-fold, from about 400-fold to about 700-fold, from about 500-fold to about 800-fold, or from about 600-fold to about 900-fold) within that mammal. In some cases, administering one or more non-nucleoside RNA polymerase inhibitors to a mammal having ZIKV viremia can be effective to reduce a ZIKV genome copy number within a mammal. In some cases, administering one or more non-nucleoside RNA polymerase inhibitors to a mammal having ZIKV viremia can be effective to reduce PFU of ZIKV virus within a mammal.

Any appropriate method can be used to determine the presence, absence, or amount of ZIKV in a mammal. For example, RT-qPCR can be used to determine the presence, absence, or amount of ZIKV in a mammal.

In some cases, treating a mammal having, or at risk of developing, ZIKV viremia (e.g., a ZIKV infection) as described herein (e.g., by administering one or more non-nucleoside RNA polymerase inhibitors such as TPB to the mammal) can be effective to reduce the severity of the ZIKV infection and/or to reduce or eliminate one or more symptoms of the ZIKV infection. In some cases, when a mammal is a pregnant mammal (e.g., a pregnant human), one or more symptoms can affect the mammal's fetus (e.g., in utero) and/or can affect the mammal's child (e.g., after birth such as a newborn child). Examples of symptoms of a ZIKV infection can include, without limitation, fever, rash (e.g., maculopapular rash), muscle pain, joint pain, conjunctivitis, vomiting, headache, and congenital Zika syndrome (e.g., including, but not limited to, microcephaly, decreased brain tissue, damage to the back of the eye such as scarring and/or pigment changes, joints with limited range of motion such as clubfoot, and/or too much muscle tone restricting body movement soon after birth). In some cases, a symptom of ZIKV infection can be as described elsewhere (see, e.g., www.cdc.gov/zika/symptoms/index.html). For example, treating a pregnant mammal (e.g., a pregnant human), having, or at risk of developing, ZIKV viremia (e.g., a ZIKV infection) as described herein (e.g., by administering one or more non-nucleoside RNA polymerase inhibitors such as TPB to the mammal) can be effective to reduce or eliminate microcephaly in the mammal's fetus and/or the mammal's child (e.g., after birth).

In some cases, one or more non-nucleoside RNA polymerase inhibitors (e.g., TPB) can be administered to a mammal having, or at risk of developing, ZIKV viremia (e.g., a ZIKV infection) in the absence of any carriers (e.g., additives, fillers, vehicles, and/or diluents).

In some cases, one or more non-nucleoside RNA polymerase inhibitors (e.g., TPB) can be formulated into a composition (e.g., a pharmaceutically acceptable composition) for administration to a mammal having, or at risk of developing, ZIKV viremia (e.g., a ZIKV infection). For example, one or more non-nucleoside RNA polymerase inhibitors can be formulated together with one or more pharmaceutically acceptable carriers (e.g., additives, fillers, vehicles, and/or diluents). In some cases, pharmaceutically acceptable carrier can be non-naturally occurring. Pharmaceutically acceptable carriers that can be used in a pharmaceutical composition described herein include, without limitation, dextrose, methanol, dimethyl sulfoxide (DMSO), ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, and wool fat.

In some cases, a composition including one or more non-nucleoside RNA polymerase inhibitors (e.g., TPB) to be administered to a mammal (e.g., a human) in need thereof (e.g., a mammal having, or at risk of developing, ZIKV viremia) can include one or more non-nucleoside RNA polymerase inhibitors as the sole active ingredient. For example, TPB can be administered to a mammal having, or at risk of developing, ZIKV viremia (e.g., a ZIKV infection) as the sole active ingredient used to treat the mammal.

In some cases, a composition including one or more non-nucleoside RNA polymerase inhibitors (e.g., TPB) to be administered to a mammal (e.g., a human) in need thereof (e.g., a mammal having, or at risk of developing, ZIKV viremia) can include one or more non-nucleoside RNA polymerase inhibitors together with one or more additional active ingredients (e.g., active ingredients that can be used to treat a mammal having, or at risk of developing, ZIKV viremia). Examples of additional active ingredients that can be used to treat a mammal having, or at risk of developing, ZIKV viremia (e.g., a ZIKV infection) that can be used to treat a ZIKV infection include, without limitation, antihistamines (e.g., chlorphenamine), corticosteroids (e.g., hydrocortisone), fever reducers (e.g., acetaminophen), immunosuppressants (e.g., mycophenolic acid), and antiparasitics (e.g., ivermectin).

A composition including one or more non-nucleoside RNA polymerase inhibitors (e.g., TPB) can be designed for any route of administration. For example, a composition including one or more non-nucleoside RNA polymerase inhibitors can be designed for parenteral (e.g., intraperitoneal) administration. Compositions suitable for parenteral administration include, without limitation, aqueous and non-aqueous sterile injection solutions that can contain anti-oxidants, buffers, bacteriostats, and solutes that render the formulation isotonic with the blood of the intended recipient. For example, a composition including one or more non-nucleoside RNA polymerase inhibitors can be designed for oral administration. Compositions suitable for oral administration include, without limitation, liquids, tablets, capsules, pills, powders, gels, and granules. In some cases, a composition including one or more non-nucleoside RNA polymerase inhibitors can be formulated for oral administration.

A composition including one or more non-nucleoside RNA polymerase inhibitors (e.g., TPB) can be designed for any type of release (e.g., release of the one or more non-nucleoside RNA polymerase inhibitors from the composition) into the mammal the composition is administered to (e.g., a mammal having, or at risk of developing, ZIKV viremia). For example, a composition including one or more non-nucleoside RNA polymerase inhibitors can be designed for immediate release, slow release, or extended release.

A composition including one or more non-nucleoside RNA polymerase inhibitors (e.g., TPB) can be administered to a mammal (e.g., a human) in need thereof (e.g., a mammal having, or at risk of developing, ZIKV viremia) in any appropriate dose(s). Effective doses can vary depending on the level of ZIKV viremia, the risk of developing ZIKV infection, the route of administration, the age and general health condition of the mammal, excipient usage, the possibility of co-usage with other therapeutic treatments such as use of other agents, and the judgment of the treating physician. For example, in cases where a composition includes TPB, the composition can include from about 5 mg TPB per kilogram (kg) body weight of the mammal being treated to about 25 mg TPB per kg body weight of the mammal being treated (e.g., from about 7 mg/kg to about 25 mg/kg, from about 10 mg/kg to about 25 mg/kg, from about 12 mg/kg to about 25 mg/kg, from about 15 mg/kg to about 25 mg/kg, from about 18 mg/kg to about 25 mg/kg, from about 20 mg/kg to about 25 mg/kg, from about 22 mg/kg to about 25 mg/kg, from about 5 mg/kg to about 23 mg/kg, from about 5 mg/kg to about 20 mg/kg, from about 5 mg/kg to about 17 mg/kg, from about 5 mg/kg to about 15 mg/kg, from about 5 mg/kg to about 12 mg/kg, from about 5 mg/kg to about 10 mg/kg, from about 5 mg/kg to about 8 mg/kg, from about 8 mg/kg to about 22 mg/kg, from about 10 mg/kg to about 20 mg/kg, from about 12 mg/kg to about 17 mg/kg, from about 10 mg/kg to about 15 mg/kg, or from about 15 mg/kg to about 20 mg/kg TPB). In some cases, a composition including TPB can include about 25 mg/kg TPB. For example, in cases where a composition includes TPB, the composition can be effective to achieve from about 100 ng of TPB per milliliter (mL) plasma in the mammal being treated to about 1000 ng of TPB per mL plasma in the mammal being treated (e.g., a plasma concentration of from about 200 ng/mL to about 1000 ng/mL, from about 250 ng/mL to about 1000 ng/mL, from about 275 ng/mL to about 1000 ng/mL, from about 300 ng/mL to about 1000 ng/mL, from about 350 ng/mL to about 1000 ng/mL, from about 400 ng/mL to about 1000 ng/mL, from about 450 ng/mL to about 1000 ng/mL, from about 500 ng/mL to about 1000 ng/mL, from about 550 ng/mL to about 1000 ng/mL, from about 600 ng/mL to about 1000 ng/mL, from about 650 ng/mL to about 1000 ng/mL, from about 700 ng/mL to about 1000 ng/mL, from about 750 ng/mL to about 1000 ng/mL, from about 800 ng/mL to about 1000 ng/mL, from about 850 ng/mL to about 1000 ng/mL, from about 900 ng/mL to about 1000 ng/mL, from about 100 ng/mL to about 900 ng/mL, from about 100 ng/mL to about 800 ng/mL, from about 100 ng/mL to about 700 ng/mL, from about 100 ng/mL to about 600 ng/mL, from about 100 ng/mL to about 500 ng/mL, from about 100 ng/mL to about 400 ng/mL, from about 100 ng/mL to about 300 ng/mL, from about 200 ng/mL to about 900 ng/mL, from about 300 ng/mL to about 800 ng/mL, from about 400 ng/mL to about 700 ng/mL, from about 500 ng/mL to about 600 ng/mL, from about 200 ng/mL to about 400 ng/mL, from about 400 ng/mL to about 600 ng/mL, or from about 600 ng/mL to about 800 ng/mL TPB). In some cases, a composition including TPB can achieve a plasma concentration of greater than 500 ng/mL TPB (e.g., a plasma concentration of about 550 ng/mL, about 600 ng/mL, about 650 ng/mL, about 700 ng/mL, about 750 ng/mL, about 800 ng/mL, about 850 ng/mL, about 900 ng/mL, or about 950 ng/mL TPB). An effective amount of a composition including one or more non-nucleoside RNA polymerase inhibitors can be any amount that reduces the severity and/or reduces or eliminates one or more symptom of a ZIKV infection without producing significant toxicity to the mammal. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, level of ZIKV viremia, severity of the ZIKV infection, and risk of developing a ZIKV infection may require an increase or decrease in the actual effective amount administered.

A composition including one or more non-nucleoside RNA polymerase inhibitors (e.g., TPB) can be administered to a mammal (e.g., a human) in need thereof (e.g., a mammal having, or at risk of developing, ZIKV viremia) in any appropriate frequency. The frequency of administration can be any frequency that reduces the severity of the ZIKV infection and/or reduces or eliminates one or more symptoms of the ZIKV infection without producing significant toxicity to the mammal. For example, the frequency of administration can be from about once a day to about ten times a day, from about three times a day to about eight times a day, or from about four times a day to about six times a day. The frequency of administration can remain constant or can be variable during the duration of treatment. As with the effective amount, various factors can influence the actual frequency of administration used for a particular application. For example, the effective amount, duration of treatment, use of multiple treatment agents, route of administration, level of ZIKV viremia, severity of the ZIKV infection, and risk of developing a ZIKV infection may require an increase or decrease in administration frequency.

A composition including one or more non-nucleoside RNA polymerase inhibitors (e.g., TPB) can be administered to a mammal (e.g., a human) in need thereof (e.g., a mammal having, or at risk of developing, ZIKV viremia) for any appropriate duration. An effective duration for administering a composition including one or more biguanides can be any duration that reduces the severity of the ZIKV infection and/or reduces or eliminates one or more symptoms of the ZIKV infection without producing significant toxicity to the mammal. For example, the effective duration can vary from several days to several months or years to a lifetime. In some cases, the effective duration for the treatment of mammal in need thereof can range in duration from about 2 days to about a week. Multiple factors can influence the actual effective duration used for a particular treatment. For example, an effective duration can vary with the frequency of administration, effective amount, use of multiple treatment agents, route of administration, level of ZIKV viremia, severity of the ZIKV infection, and risk of developing a ZIKV infection.

In some cases, methods described herein also can include administering to a mammal in need thereof (e.g., a mammal having, or at risk of developing, ZIKV viremia) one or more additional treatments used to treat a mammal having, or at risk or developing, ZIKV viremia (e.g., a ZIKV infection). The one or more additional treatments used to treat a ZIKV infection can include any appropriate treatment. In some cases, a ZIKV infection treatment can include getting plenty of rest. In some cases, a ZIKV infection treatment can include drinking fluids (e.g., to prevent dehydration). In some cases, a ZIKV infection treatment can include not taking aspirin and/or other non-steroidal anti-inflammatory drugs (NSAIDS). In some cases, a ZIKV infection treatment can include administration of one or more pharmacotherapies such as antibiotics (e.g., metronidazole and dexamethasone), anti-histamines (e.g., chlorphenamine), corticosteroids (e.g., hydrocortisone), and/or fever reducers (e.g., acetaminophen). For example, a mammal having, or at risk of developing, ZIKV viremia (e.g., a ZIKV infection) can be administered one or more non-nucleoside RNA polymerase inhibitors (e.g., TPB) and can be administered one or more additional treatments used to treat a ZIKV infection. In cases where a mammal having, or at risk of developing, ZIKV viremia (e.g., a ZIKV infection) is treated with one or more non-nucleoside RNA polymerase inhibitors and is treated with one or more additional agents used to treat a ZIKV infection, the additional treatment used to treat a ZIKV infection can be administered at the same time or independently. For example, when administered independently, the one or more non-nucleoside RNA polymerase inhibitors can be administered first, and the one or more additional treatment used to treat a ZIKV infection can be administered second, or vice versa.

In certain instances, a course of treatment and the severity of one or more symptoms related to the condition being treated (e.g., a ZIKV infection) can be monitored. Any appropriate method can be used to determine whether or not the severity of one or more symptoms is reduced or eliminated. For example, the severity of a ZIKV infection can be assessed using any appropriate methods and/or techniques, and can be assessed at different time points. For example, physical examinations can be used to determine the severity of one or more symptoms of a ZIKV infection.

In some cases, one or more non-nucleoside RNA polymerase inhibitors (e.g., TPB) can be used to treat a mammal having a disease or disorder associated with a ZIKV infection. Examples of diseases and disorders associated with a ZIKV infection include, without limitation, Guillain-Barre syndrome.

In some cases, one or more non-nucleoside RNA polymerase inhibitors (e.g., TPB) can be used to treat a mammal having, or at risk of developing, one or more additional infections caused by a member of the Flaviviridae family, which includes Dengue viruses, West Nile viruses, yellow fever viruses, and Japanese encephalitis viruses.

This document also provides kits that can be used for a variety of applications including, without limitation, diagnosing a mammal as having, or as being at risk of developing, ZIKV viremia (e.g., a ZIKV infection); treating a mammal having, or at risk of developing, ZIKV viremia (e.g., a ZIKV infection); and/or preparing a composition (e.g., by combining reagents) for use in diagnosing and/or treating a mammal having, or at risk of developing, ZIKV viremia (e.g., a ZIKV infection). In some cases, a kit provided herein can include one or more non-nucleoside RNA inhibitors (e.g., TPB) as described herein. For example, a kit can include a composition (e.g., a pharmaceutically acceptable composition) including one or more non-nucleoside RNA inhibitors. For example, a kit can include one or more non-nucleoside RNA inhibitors and one or more pharmaceutically acceptable carriers (e.g., additives, fillers, vehicles, and/or diluents) for preparing and/or administering a composition (e.g., a vaccine composition). In some cases, a kit provided herein can include reagents that can be used to detect ZIKV infections. For example a kit provided herein can be designed as a diagnostic kit. For example, a kit provided herein can be designed as a kit to monitor treatment of a mammal having, or at risk of developing, ZIKV viremia (e.g., a ZIKV infection). For example, a kit provided herein can be designed to include reagents that can be used to detect the presence of a ZIKV genome, or a portion thereof, and/or the presence of one or more ZIKV polypeptides in samples (e.g., fluid samples such as blood and urine) obtained from a mammal. In some cases, a kit provided herein also can include packaging. In some cases, a kit provided herein also can include, instructions for use. For example, instructions for use can be provided as a separate component within the kit and/or printed directly on any packaging (e.g., packaging for the kit or packaging for a component within the kit).

The invention will be further described in the following examples, which do not limit the scope of the invention described in the claims.

EXAMPLES

Example 1: Discovery of a Non-Nucleoside RNA Polymerase Inhibitor for Blocking Zika Virus Replication Through in Silico Screening Materials and Methods
Compounds Ten lead compounds (Table 1) were purchased from Hit2Lead Company (ChemBridge Corporation, San Diego, Calif.). Each compound was dissolved in dimethyl sulfoxide (DMSO) to prepare stock solutions of 10 mM and 1 mM and was stored at −20° C. The compound 1 (c1) used in this research is 3-chloro-N-[({4-[4-(2-thienylcarbonyl)-1-piperazinyl]phenyl}amino)carbonothioyl]-1-benzothiophene-2-carboxamide (TPB). Based on 1H NMR and LC-MS (ELSD, DAD 200-400 nm, MSD APCI positive) analyses by the provider, the compound is ≥95% pure. Mycophenolic acid (MPA) and Ivermectin (IVM) were purchased from Sigma (St. Louis, Mo.) and resuspended in DMSO to prepare stock solutions. All the compounds used have ≥95% purity.

TABLE 1

Docking scores of the top 10 compounds.

| Compound | Molecular Weight | Score |
|---|---|---|
| 1 | 541.108 | −118.794 |
| 2 | 455.528 | −118.36 |
| 3 | 525.572 | −118.358 |
| 4 | 516.638 | −118.097 |
| 5 | 476.480 | −117.319 |
| 6 | 539.618 | −116.087 |
| 7 | 484.618 | −115.823 |
| 8 | 471.592 | −115.789 |
| 9 | 471.574 | −115.724 |
| 10 | 482.443 | −114.333 |

Cells and Viruses

Vero (Cercopithecus aethiops, CCL-81), HTR-8/SVneo human trophoblast (CRL-3271), and NTERA-2 human embryonal carcinoma (CRL-1973) cells were obtained from ATCC. The cells were grown and maintained in Dulbecco's modified Eagle's medium (DMEM) containing 10% heat-inactivated fetal bovine serum (FBS) and penicillin/streptomycin (PS) in humidified chamber with 5% CO2 at 37° C. Zika virus strain PRVABC59 and MR766 were obtained from Barbara Johnson and Brandy Russell at the Centers for Disease Control and Prevention, Fort Collins, Colo., USA. The viruses were passaged once in Vero cells to prepare stocks and were stored at −80° C. in small aliquots. Titers of the stock viruses were determined by plaque assay using Vero cells as described elsewhere (see, e.g., Annamalai et al., 2017 *J. Virol.* 91:e01348-17).

Molecular Modeling and in Silico Screening

The ZIKV RdRp structure was modeled based on sequence homology using Modeller 9 program (Webb and Sali, 2014). The DENV-3 RdRp structure (PDB: 2J7U) was used as the template. In silico screening was performed using Molegro Virtual Docker (MVD) (Molegro ApS, Aarhus, Denmark). The docking site was defined using a ray-tracing algorithm. This resulted in a cavity with a volume of approximately 1034 cubic Å. A receptor grid was built within this cavity with a resolution of 0.2 Å and a radius of 13 Å from the geometric center of the cavity in the ZIKV RdRp model. A 100,000 compound library from Chem-Bridge (Chembridge DIVERSet™ Chemical Library, ChemBridge Corporation, San Diego, Calif.) was used for this virtual screening. All structural analysis were conducted in the Discovery Studio 4.0 (Biovia, San Diego, Calif.).

Inhibition Assays

Vero cells were seeded in a 96-well plate with the density of 6000 cells per well. In the initial screening study, the compound (1 μM)-virus (0.1 PFU/cell) mixture in virus growth medium (VGM) [DMEM containing 2% FBS, PS, 20 mM hydroxyethyl piperazine ethane sulfonic acid (HEPES), 1 mM sodium pyruvate, and non-essential amino acids] was added to the cells and incubated for 72 h. In a separate experiment conducted using 12-well plates, the cells were first infected with the virus at 0.1 PFU/cell and following adsorption, the cells were washed twice in PBS and incubated in VGM containing 1 μM concentrations of the drugs. The cell culture media were collected at 72-96 h post-infection and assayed for infectious virus by plaque assay and viral genome copies by quantitative RT-PCR (RT-qPCR). In all subsequent studies, cells in 12-well plates were infected with ZIKV at MOI of 0.1 PFU/cell and following virus adsorption for 1 h at 37° C., VGM containing various concentrations TPB was added to the cells and incubated as above. Clarified supernatants from the infected cells were then used to determine infectious virus or genome copies as above.

ATP-Based Cell Viability Assay

A modified ATP based cytopathic effect (CPE) assay was used for this study based on the CPE method for anti-DENV drug development described elsewhere (see, e.g., Che et al., 2009 *Int. J. Clin. Exp. Med.* 2:363-373). Vero cells (approximately 30,000 per well) were seeded in a black 96-well plate for 24 hours before the experiment. Cell monolayers were treated with various concentrations of the drugs for 4 days at 37° C. The ATP concentration was measured following manufacturer's recommendations using CellTiter-Glo kit from Promega (Madison, Wis.). Luminescence was recorded using a Veritas Microplate Luminometer at 420 nm. The 50% cytotoxic concentration ($CC_{50}$) was calculated by a non-linear regression analysis of the dose-response curves.

Quantitative Real Time RT-PCR

ZIKV viral RNA was detected using RT-qPCR on a C100 Thermal Cycler and the CFX96 Real-Time system (Bio-Rad). Viral RNA (vRNA) was extracted from culture supernatant using a QIAamp Viral RNA Mini kit (Qiagen) and TaqMan Fast Virus 1-Step Master Mix (Life technologies). ZIKV primers and probe (ZIKF: CCGCTGCC-CAACACAAG (SEQ ID NO:1); ZIK-R: CCACTAACGTTCTTTTGCAGACAT (SEQ ID NO:2); PCR Probe: ZIK-P: AGCCTACCTTGACAAGCAATCA-GACACTCAA (SEQ ID NO:3)) were used for quantitative RT-PCR (RT-qPCR) with the following parameters: 50° C. 30 min, 95° C. 5 min, (95° C. 30 S, 58° C. 1 min)×40 cycles. RNA standard concentrations were determined based on the back calculation with OD values and molecular weights and were generated through serial dilution with $R^2 > 0.95$.

Pharmacokinetic (PK) Study Design

For PK studies, groups of Balb/C mice (n=3) were injected intraperitoneally with doses of 5 mg/kg or 25 mg/kg of body weight of TPB in 5% dextrose, plasma was collected from the animals at various times post-injection and stored at −80° C. until analysis by LC-MS/MS for TPB concentrations. Plasma drug levels were subjected to noncompartmental analysis (WinNonlin ver. 6.4 Certera Inc., Princeton, N.J.). The predicted steady-state levels>500 ng/ml were estimated using a twelve h dosing of 25 mg/kg dose of the compound in mice.

Determination of Drug Concentration in Plasma

TPB was dissolved in DMSO at 1 mg/ml. Working standard solutions were then prepared in 50% methanol in water from the stock solution. Standards (an eight-point calibration curve) and quality controls (at three levels) were prepared by spiking the working standard solutions to blank mouse plasma. One hundred μl aliquot of plasma was mixed with 25 μl of internal standard spiking solution (rilpivirine 1000 ng/ml in 50% acetonitrile in water), 1.5 ml ethyl acetate was added and vortexed vigorously for 15 min. The tubes were centrifuged at 1700×g for 5 min and 1.3 ml supernatant was evaporated to dryness under a stream of nitrogen at 40° C. The dried extract was reconstituted with 0.1 ml of 50% acetonitrile in water and 5 μl was injected into the LCMS/MS instrument. The dynamic range of the method was 25-4000 ng/ml.

An Agilent 1200 HPLC system (Agilent Technologies, CA, USA) coupled with AB Sciex API 3200 Q Trap with an electrospray ionization source (Applied Biosystems, Foster City, Calif., USA) was used. The mass transitions m/z 541.2→330.2 and 541.2→212.2 for analyte and m/z 367.2→195.2 for internal standard were monitored. Chromatographic separation was carried out on Phenomenex Synergi Polar-RP (150×2.0 mm, 4µ) column with isocratic mobile phase consisting of 0.1% formic acid in water (A) and 0.1% formic acid in acetonitrile (B) (20:80 v/v) at a flow rate of 0.5 ml/min. The retention times of analyte and internal standard were 2 and 1.2 min respectively.

Viral Inhibition Test in Mice

Balb/C mice were obtained from the Jackson Laboratory (Bar Harbor, Me., USA). After acclimatization for four days, groups of animals (n=6 per group) were injected intraperitoneally with 25 mg/kg body weight dose of TPB diluted in saline or saline alone (no drug control). Following three injections at 12 h intervals, 500 PFU of PRVABC59 virus diluted in PBS was inoculated into each mouse by the subcutaneous (SC) route. Blood was collected by retro-orbital bleeding under anesthesia at days 2, 3, 4, 5, and 6 post-infection. Viral genome copies in the plasma were determined by RT-qPCR.

Statistical Analysis

Data were analyzed using GraphPad Prism software version 6.0. Unpaired two-tailed Student's t-test for pairwise comparison between the groups to determine significant differences in viral loads (RNA levels and infectious titer) was performed. Data were represented as means (±SEM).

Results

In Silico Screening of a Compound Library Against ZIKV Polymerase (RdRp) Loops

Since the crystal structure of ZIKV RdRp was not available when this project was initiated, we generated a three-dimensional model of ZIKV RdRp through structural modeling based on the analog of DENV-3 RdRp structure (PDB: 2J7U). The choice of the DENV-3 RdRP structure as the template was due to its high level of protein sequence homology (65% identity and 78% similarity) and the high resolution (1.8 □) of the structure. The predicted ZIKV RdRp structure superimposed closely with a recently solved crystal structure (see, e.g., Duan et al., 2017 *EMBO J.* 36:919-933) of ZIKV RdRp (FIG. 8) with C-alpha atom RMSD of 2.519. The target site appears to fit well and the relative larger RMSD value should be mainly from the flexible loops and the outer layers of the three domains. Like RdRp structures in other flaviviruses, the ZIKV RdRp structure model showed a very similar right-handed architecture with fingers, palm and thumb subdomains (FIG. 1A). Subsequently, we conducted in silico screening of a library of 100,000 small molecule compounds against the catalytic active site on the ZIKV RdRp molecule. The active site is in the palm subdomain which is critical for de novo RNA synthesis performed by ZIKV RdRp. Based on the in silico screening data, the top 10 compounds with highest docking scores are shown in Table 1. The molecular weights of these compounds are also similar (around 500 Da) which are in the appropriate range of druggable compounds.

Cell-Based Inhibition Test of the Lead Compounds Against ZIKV Infection

Examination of PRVABC59 ZIKV growth in Vero cells in the presence of 1 μM concentrations of the compounds (c1-c10) showed that c1, 3-chloro-N-[({4-[4-(2-thienylcarbonyl)-1-piperazinyl]phenyl}amino)carbonothioyl]-1-benzothiophene-2-carboxamide (TPB, FIG. 1B), exhibited the highest inhibitory activity among the 10 lead compounds tested. While the ZIKV growth was inhibited (as determined by genome copies in the culture supernatants) by >99% in cells treated with TPB compared to the vehicle-only treated cells (FIG. 2A), c6 and c10 also inhibited virus growth by nearly 70-80%. Infectious virus yield was inhibited by at least 1000-fold in the presence of 1 μM c1 (FIG. 2B) whereas c6 and c10 inhibited the yield by nearly 10-fold at the same concentrations. Although the majority of the compounds could be readily seen bound to the target site, c1, c6, and c10 appeared to have made additional contacts with the priming loop as well as other regions in the RdRp target site (FIG. 9). From molecular docking analysis, it appears that c1 interacts with residues in the target site of the viral RdRp (FIG. 1C-D). Three hydrogen bonds of TPB are in direct contact with two aspartic acid residues (D535 in motif A and D665 in motif C) in RdRp (FIG. 1C). Since these two aspartic acid residues as well as D665 are highly conserved residues in the target and active site of all RdRps of flaviviruses and play critical roles in coordinating divalent metal ions (Mg++), TPB could potentially be a highly promising anti-ZIKV as well as anti-flavivirus drug candidate. So, from the initial cursory screening studies, TPB was shown to inhibit ZIKV replication significantly.

We then tested the inhibitory activity of TPB in a dose-dependent manner in the μM range. The results show that even at 0.5 μM concentration of TPB, significant inhibitory activity against ZIKV replication was observed. Both genome copy numbers (FIG. 3A) and infectious virus (FIG. 3B) in the supernatants were reduced by over 100-fold at this concentration of TPB. Although TPB at 1 μM reduced virus growth by over 1000-fold, further increase in TPB concentration did not result in further inhibition (FIG. 3A-B). Viral E protein synthesis in infected cells was also significantly inhibited at 0.5 μM TPB and was undetectable at higher concentrations (FIG. 3C). These results suggest that TPB is a potent inhibitor of ZIKV replication.

ZIKV Growth Inhibition of by TPB

Since we used the contemporary isolate of ZIKV (PRVABC59, isolated from a patient in Puerto Rico in 2015) in our initial studies, we wanted to determine if TBP also has antiviral activity against the historical isolate of the virus. Our results suggest that the MR766 Ugandan isolate was also sensitive to inhibition by TPB at the concentrations tested (FIG. 4A). The extent of MR766 virus growth inhibition appeared to be similar to that of the PRVABC59 virus (FIGS. 3 and 4A). Overall, it appears that maximal ZIKV growth inhibition by TPB could be achieved at 1 or 2 μM concentrations and further increase had no significant inhibitory effect, indicating that the TPB inhibitory target is saturable at these concentrations. In addition, not only TPB inhibited ZIKV growth in Vero cells (FIG. 3), but also it inhibited the virus growth in other cells such as human trophoblast cell line HTR-8 (FIG. 4B) as well as the human testicular cell line NTERRA (FIG. 4C) that are known to be the targets of ZIKV infection in humans. Overall, these studies suggest that TBP inhibits both the contemporary and historical isolates of the virus and that the inhibition is not cell-type dependent.

Characterization of TPB Antiviral Activity In Vitro: IC50 and CC50

Inhibitory Concentration 50 (IC50) Determination.

To characterize the anti-ZIKV potency of TPB, we conducted studies to determine the inhibitory concentration 50 (IC50). We used serial 2-fold dilutions of TPB and treated the Vero cells infected with PRVABC59. The culture supernatants were assayed for infectious virus by plaque assay and expressed as % virus yield relative to the virus yield without TPB. The data were statistically analyzed and the IC50 concentration was determined to be about 94 nM (FIG. 5A). The IC50 value of TPB in the 10-100 nM range also suggests that TPB is a strong inhibitor of ZIKV and a potential drug candidate for further development.

Cellular Cytotoxicity 50 (CC50) Determination.

Low level of cellular cytotoxicity is an essential criterion for drug development. It also suggests whether the drug's inhibitory effect is independent of cellular cytotoxicity due to the presence of the drug. Therefore, we conducted cell viability assay to determine the cellular cytotoxicity 50 (CC50) concentration of TPB. Our results show that CC50 of TPB is 19.4 µM (FIG. 5B). The selectivity index 50 (SI50, CC50/IC50) is calculated to be 206. This high SI50 also suggests that TBP is not only a potent inhibitor of ZIKV at sub-micromolar concentrations but is also nontoxic to the cells.

Comparison of TPB Inhibition with Other Known Inhibitors of ZIKV.

To further compare the potency of TPB relative to other identified ZIKV inhibitors, two inhibitors were examined that have been recently shown to inhibit ZIKV replication. Mycophenolic acid (MPA) is an immunosuppressant drug used to prevent rejection in organ transplantation and was shown to inhibit DENV RNA replication (see, e.g., Diamond et al., 2002 Virology 304:211-221). In a screen of FDA-approved drugs for inhibition of ZIKV infection, MPA at 1 µM was found to inhibit infection of cells in vitro by ZIKV by over 99% (see, e.g., Barrows et al., 2016 Cell Host Microbe 20:259-270). Likewise, Ivermectin (IVM), an anti-parasitic drug was found to inhibit ZIKV infection strongly at 10 µM (see, e.g., Barrows et al., 2016 Cell Host Microbe 20:259-270). A side-by-side comparison of the inhibitory potency of TPB with MPA and IVM shows that while TPB inhibited ZIKV yield by over 1000-fold, MPA and IVM inhibited virus yield by approximately 10- to 20-fold (FIG. 6). These results suggest that TPB is more potent in inhibiting ZIKV as compared to MPA or IVM.

Antiviral Activity of TPB In Vivo

Since TPB was found to be a potent inhibitor of ZIKV replication in vitro, we wanted to examine if it also inhibits virus replication and viremia in an immunocompetent mouse model. Therefore, a pharmacokinetics (PK) analysis of TPB in immunocompetent Balb/C mice was conducted to examine the stability and in vivo retention of the drug. The results of PK studies suggest that TPB is retained in the mouse plasma at approximately 100 ng/ml level 10-12 h post-injection at the two doses tested (FIG. 7A). Based on non-compartment analysis of the data, it was estimated that steady-state levels>500 ng/ml of TPB (~1 µM) could be achieved using a twelve hour dosing at 25 mg/kg dose of the compound in mice. To examine the effect of the drug on ZIKV growth in mice, groups of mice (n=6) were injected with the drug at 25 mg/kg dose and subsequently infected with 500 PFU of ZIKV. Virus load in the plasma of the animals at 24 hour intervals was determined. Results of virus growth (genome copies) in individual animals (FIG. 7B) show that these immunocompetent mice supported transient ZIKV growth and the level of viral RNA detected on day 4 post-infection was nearly 40-fold lower in mice injected with the drug as compared to the group injected with the vehicle (5% dextrose) alone (FIG. 7C). The level of TPB in the plasma on average reached nearly 270 ng/ml by 2 days post-infection (FIG. 7D). Although this level of TPB was not optimal for maximal virus growth inhibition as observed under in vitro conditions, the results suggest that TPB exerts significant growth inhibition of ZIKV in vivo.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for treating a mammal having Zika virus (ZIKV) viremia, said method comprising: administering to said mammal a composition comprising a non-nucleoside RNA polymerase inhibitor, wherein said non-nucleoside RNA polymerase inhibitor is 3-chloro-N-[({4-[4-(2-thienylcarbonyl)-1-piperazinyl]phenyl}amino)carbonothioyl]-1-benzothiophene-2-carboxamide (TPB).

2. The method of claim 1, wherein said mammal is a human.

3. The method of claim 1, wherein said non-nucleoside RNA polymerase inhibitor can bind to a catalytic active site of an RNA-dependent RNA-polymerase (RdRp) of said ZIKV to inhibit ZIKV replication.

4. The method of claim 1, wherein said non-nucleoside RNA polymerase inhibitor has an inhibitory concentration 50 (IC50) of from about 10 nM to about 200 nM.

5. The method of claim 1, wherein said non-nucleoside RNA polymerase inhibitor has a cytotoxicity concentration 50 (CC50) of from about 15 µM to about 25 µM.

6. The method of claim 1, wherein said non-nucleoside RNA polymerase inhibitor has a selective index 50 (SI50) of about 206.

7. The method of claim 1, wherein said administering step is performed prior to said mammal developing a ZIKV infection.

8. The method of claim 1, wherein said administering step is performed after mammal has developed a ZIKV infection.

9. The method of claim 1, wherein said non-nucleoside RNA polymerase inhibitor is administered intraperitoneally, intravenously, intramuscularly, or subcutaneously.

10. A method of preventing microcephaly in a fetus said method comprising: administering a composition comprising a non-nucleoside RNA polymerase inhibitor to a mammal pregnant with said fetus, wherein said mammal has a ZIKV infection, wherein said non-nucleoside RNA polymerase inhibitor is 3-chloro-N-[({4-[4-(2-thienylcarbonyl)-1-piperzinyl]phenyl}amino)carbonothioyl]-1-benzothiophene-2-carboxamide (TPB).

11. The method of claim 10, wherein said mammal is a human.

12. A method of treating an adult mammal having Guillain-Barre syndrome said method comprising: administering to said mammal a composition comprising a non-nucleoside RNA polymerase inhibitor, wherein said mammal has a ZIKV infection, wherein said non-nucleoside RNA polymerase inhibitor is 3-chloro-N-[({4-[4-(2-thienylcarbonyl)-1-piperazinyl]phenyl}amino)carbonthioyl]-1-benzothiophene-2-carboxamide (TPB).

13. The method of claim 12, wherein said mammal is a human.

14. The method of claim 10, wherein said non-nucleoside RNA polymerase inhibitor can bind to a catalytic active site of an RNA-dependent RNA-polymerase (RdRp) of said ZIKV to inhibit ZIKV replication.

15. The method of claim 10, wherein said non-nucleoside RNA polymerase inhibitor is administered intraperitoneally, intravenously, intramuscularly, or subcutaneously.

16. The method of claim 12, wherein said non-nucleoside RNA polymerase inhibitor can bind to a catalytic active site of an RNA-dependent RNA-polymerase (RdRp) of said ZIKV to inhibit ZIKV replication.

17. The method of claim 12, wherein said non-nucleoside RNA polymerase inhibitor is administered intraperitoneally, intravenously, intramuscularly, or subcutaneously.

* * * * *